(12) United States Patent
Niemiec et al.

(10) Patent No.: US 12,310,643 B2
(45) Date of Patent: May 27, 2025

(54) ALIGNING VERTEBRAL BODIES

(71) Applicant: GLOBUS MEDICAL, INC., Audubon, PA (US)

(72) Inventors: Marcin Niemiec, Norristown, PA (US); Duncan Sibson, Malvern, PA (US); Noah Hansell, King of Prussia, PA (US); Chad Glerum, Pennsburg, PA (US); Colm McLaughlin, Glenside, PA (US); Daniel Davenport, Collegeville, PA (US); Mark Weiman, Downingtown, PA (US); Jason Gray, East Greenville, PA (US); Khiem Pham, Chalfont, PA (US); Michael Black, Phoenixville, PA (US); Ben Silber, Flemington, NJ (US); Mark Fromhold, Phoenixville, PA (US); Andrew Iott, Newtown Square, PA (US); Kathleen Hill, Newtown Square, PA (US); John Gilbert, Douglassville, PA (US); Richard Castle, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/321,966

(22) Filed: May 23, 2023

(65) Prior Publication Data

US 2024/0325064 A1 Oct. 3, 2024

Related U.S. Application Data

(63) Continuation of application No. 16/739,424, filed on Jan. 10, 2020, now Pat. No. 11,730,528, which is a
(Continued)

(51) Int. Cl.
*A61F 2/44* (2006.01)
*A61B 17/70* (2006.01)
(Continued)

(52) U.S. Cl.
CPC ...... *A61B 17/8866* (2013.01); *A61B 17/7059* (2013.01); *A61F 2/442* (2013.01);
(Continued)

(58) Field of Classification Search
CPC ................................. A61F 2/44–447
See application file for complete search history.

(56) References Cited

U.S. PATENT DOCUMENTS

| 5,163,949 A | 11/1992 | Bonutti |
| 5,163,960 A | 11/1992 | Bonutti |

(Continued)

FOREIGN PATENT DOCUMENTS

| FR | 2727003 A1 | 5/1996 |
| JP | 2009-512520 A | 3/2009 |

(Continued)

OTHER PUBLICATIONS

International Search Report and Written Opinion of the International Searching Authority for PCT/US2013/043246 dated Sep. 6, 2013.

(Continued)

*Primary Examiner* — Eduardo C Robert
*Assistant Examiner* — Steven J Cotroneo

(57) ABSTRACT

Misaligned bones on opposite sides of a joint are aligned using a first rigid extension securable to one of the misaligned bones using a particular surgical approach, and a second rigid extension having a contacting surface positionable in contact with the other the two misaligned bones from the same surgical approach. The first and second rigid extensions are moved with respect to each other using a (Continued)

lever, whereby a pulling force is exerted on one of the bones, and a pushing force on the other, thereby aligning the first and second misaligned bones.

16 Claims, 18 Drawing Sheets

Related U.S. Application Data continuation of application No. 13/483,558, filed on May 30, 2012, now abandoned.

(51) Int. Cl.
- *A61B 17/88* (2006.01)
- *A61F 2/46* (2006.01)
- *A61F 2/30* (2006.01)
- *A61F 2/48* (2006.01)

(52) U.S. Cl.
CPC .......... *A61F 2/4455* (2013.01); *A61F 2/4611* (2013.01); *A61F 2002/30266* (2013.01); *A61F 2002/30329* (2013.01); *A61F 2002/30331* (2013.01); *A61F 2002/30387* (2013.01); *A61F 2002/30405* (2013.01); *A61F 2002/30433* (2013.01); *A61F 2002/30448* (2013.01); *A61F 2002/30471* (2013.01); *A61F 2002/30494* (2013.01); *A61F 2002/30518* (2013.01); *A61F 2002/30523* (2013.01); *A61F 2002/30525* (2013.01); *A61F 2002/30528* (2013.01); *A61F 2002/30553* (2013.01); *A61F 2002/30556* (2013.01); *A61F 2002/30578* (2013.01); *A61F 2002/30579* (2013.01); *A61F 2002/30593* (2013.01); *A61F 2002/30604* (2013.01); *A61F 2002/30677* (2013.01); *A61F 2/30744* (2013.01); *A61F 2002/30836* (2013.01); *A61F 2/441* (2013.01); *A61F 2002/4622* (2013.01); *A61F 2002/4627* (2013.01); *A61F 2/484* (2021.08)

(56) References Cited

U.S. PATENT DOCUMENTS

| | | | |
|---|---|---|---|
| 5,197,971 A | 3/1993 | Bonutti | |
| 5,269,785 A | 12/1993 | Bonutti | |
| 5,295,994 A | 3/1994 | Bonutti | |
| 5,329,846 A | 7/1994 | Bonutti | |
| 5,331,975 A | 7/1994 | Bonutti | |
| 5,345,927 A | 9/1994 | Bonutti | |
| 5,397,364 A | 3/1995 | Kozak et al. | |
| 5,403,317 A | 4/1995 | Bonutti | |
| 5,403,348 A | 4/1995 | Bonutti | |
| 5,441,538 A | 8/1995 | Bonutti | |
| 5,454,365 A | 10/1995 | Bonutti | |
| 5,458,641 A | 10/1995 | Jiminez | |
| 5,464,426 A | 11/1995 | Bonutti | |
| 5,496,348 A | 3/1996 | Bonutti | |
| 5,514,153 A | 5/1996 | Bonutti | |
| 5,522,846 A | 6/1996 | Bonutti | |
| 5,527,343 A | 6/1996 | Bonutti | |
| 5,534,012 A | 7/1996 | Bonutti | |
| 5,545,222 A | 8/1996 | Bonutti | |
| 5,549,612 A | 8/1996 | Yapp et al. | |
| 5,549,630 A | 8/1996 | Bonutti | |
| 5,549,631 A | 8/1996 | Bonutti | |
| 5,569,305 A | 10/1996 | Bonutti | |
| 5,577,517 A | 11/1996 | Bonutti | |
| 5,584,862 A | 12/1996 | Bonutti | |
| 5,593,425 A | 1/1997 | Bonutti | |
| 5,624,462 A | 4/1997 | Bonutti | |
| 5,662,710 A | 9/1997 | Bonutti | |
| 5,667,520 A | 9/1997 | Bonutti | |
| 5,685,826 A | 11/1997 | Bonutti | |
| 5,694,951 A | 12/1997 | Bonutti | |
| 5,707,390 A | 1/1998 | Bonutti | |
| 5,716,325 A | 2/1998 | Bonutti | |
| 5,733,306 A | 3/1998 | Bonutti | |
| 5,735,875 A | 4/1998 | Bonutti | |
| 5,827,318 A | 10/1998 | Bonutti | |
| 5,845,645 A | 12/1998 | Bonutti | |
| 5,860,997 A | 1/1999 | Bonutti | |
| 5,861,041 A | 1/1999 | Tienboon | |
| 5,865,848 A | 2/1999 | Baker | |
| 5,888,196 A | 3/1999 | Bonutti | |
| 5,888,219 A | 3/1999 | Bonutti | |
| 5,888,223 A | 3/1999 | Bray, Jr. | |
| 5,928,267 A | 7/1999 | Bonutti | |
| 5,935,131 A | 8/1999 | Bonutti | |
| 5,941,900 A | 8/1999 | Bonutti | |
| 5,954,739 A | 9/1999 | Bonutti | |
| 6,010,525 A | 1/2000 | Bonutti | |
| 6,017,305 A | 1/2000 | Bonutti | |
| 6,042,596 A | 3/2000 | Bonutti | |
| 6,059,817 A | 5/2000 | Bonutti | |
| 6,066,175 A | 5/2000 | Henderson et al. | |
| 6,077,292 A | 6/2000 | Bonutti | |
| 6,086,593 A | 7/2000 | Bonutti | |
| 6,099,531 A | 8/2000 | Bonutti | |
| 6,102,928 A | 8/2000 | Bonutti | |
| 6,132,472 A | 10/2000 | Bonutti | |
| RE36,974 E | 11/2000 | Bonutti | |
| 6,156,037 A | 12/2000 | LeHuec et al. | |
| 6,159,234 A | 12/2000 | Bonutti | |
| 6,171,236 B1 | 1/2001 | Bonutti | |
| 6,171,299 B1 | 1/2001 | Bonutti | |
| 6,174,313 B1 | 1/2001 | Bonutti | |
| 6,187,023 B1 | 2/2001 | Bonutti | |
| 6,200,347 B1 | 3/2001 | Anderson et al. | |
| 6,203,565 B1 | 3/2001 | Bonutti | |
| 6,206,922 B1 | 3/2001 | Zdeblick et al. | |
| 6,217,617 B1 | 4/2001 | Bonutti | |
| 6,231,592 B1 | 5/2001 | Bonutti | |
| 6,231,610 B1 | 5/2001 | Geisler | |
| 6,258,089 B1 | 7/2001 | Campbell et al. | |
| 6,277,136 B1 | 8/2001 | Bonutti | |
| 6,287,325 B1 | 9/2001 | Bonutti | |
| 6,358,266 B1 | 3/2002 | Bonutti | |
| 6,361,565 B1 | 3/2002 | Bonutti | |
| 6,368,343 B1 | 4/2002 | Bonutti | |
| 6,383,186 B1 | 5/2002 | Michelson | |
| 6,432,106 B1 | 8/2002 | Fraser | |
| 6,447,516 B1 | 9/2002 | Bonutti | |
| 6,451,042 B1 | 9/2002 | Bonutti | |
| 6,464,713 B2 | 10/2002 | Bonutti | |
| 6,468,289 B1 | 10/2002 | Bonutti | |
| 6,468,293 B2 | 10/2002 | Bonutti | |
| 6,475,230 B1 | 11/2002 | Bonutti | |
| 6,482,233 B1 | 11/2002 | Aebi | |
| 6,500,195 B2 | 12/2002 | Bonutti | |
| 6,503,267 B2 | 1/2003 | Bonutti | |
| 6,503,277 B2 | 1/2003 | Bonutti | |
| 6,540,785 B1 | 4/2003 | Gill et al. | |
| 6,543,455 B2 | 4/2003 | Bonutti | |
| 6,558,423 B1 | 5/2003 | Michelson | |
| 6,558,424 B2 * | 5/2003 | Thalgott | A61F 2/4611 623/17.11 |
| 6,569,187 B1 | 5/2003 | Bonutti | |
| 6,575,982 B1 | 6/2003 | Bonutti | |
| 6,585,750 B2 | 7/2003 | Bonutti | |
| 6,592,531 B2 | 7/2003 | Bonutti | |
| 6,592,609 B1 | 7/2003 | Bonutti | |
| 6,607,534 B2 | 8/2003 | Bonutti | |
| 6,620,181 B1 | 9/2003 | Bonutti | |
| 6,630,000 B1 | 10/2003 | Bonutti | |
| 6,635,073 B2 | 10/2003 | Bonutti | |
| 6,638,309 B2 | 10/2003 | Bonutti | |
| 6,652,532 B2 | 11/2003 | Bonutti | |
| 6,666,889 B1 | 12/2003 | Commarmond | |
| 6,702,821 B2 | 3/2004 | Bonutti | |
| 6,702,856 B2 | 3/2004 | Bonutti | |

(56) References Cited

U.S. PATENT DOCUMENTS

| | | |
|---|---|---|
| 6,719,803 B2 | 4/2004 | Bonutti |
| 6,736,853 B2 | 5/2004 | Bonutti |
| 6,740,118 B2 | 5/2004 | Eisermann et al. |
| 6,770,078 B2 | 8/2004 | Bonutti |
| 6,776,938 B2 | 8/2004 | Bonutti |
| 6,827,740 B1 | 12/2004 | Michelson |
| 6,835,198 B2 | 12/2004 | Bonutti |
| 6,860,885 B2 | 3/2005 | Bonutti |
| 6,860,904 B2 | 3/2005 | Bonutti |
| 6,899,735 B2 | 5/2005 | Coates et al. |
| 6,905,517 B2 | 6/2005 | Bonutti |
| 6,908,466 B1 | 6/2005 | Bonutti |
| 6,932,835 B2 | 8/2005 | Bonutti |
| 6,972,019 B2 | 12/2005 | Michelson |
| 6,989,029 B2 | 1/2006 | Bonutti |
| 6,990,982 B1 | 1/2006 | Bonutti |
| 7,001,432 B2 | 2/2006 | Keller et al. |
| 7,018,416 B2 * | 3/2006 | Hanson ............... A61B 17/1671 623/17.16 |
| 7,025,787 B2 | 4/2006 | Bryan et al. |
| 7,048,755 B2 | 5/2006 | Bonutti |
| 7,070,557 B2 | 7/2006 | Bonutti |
| 7,087,073 B2 | 8/2006 | Bonutti |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti |
| 7,134,437 B2 | 11/2006 | Bonutti |
| 7,137,997 B2 | 11/2006 | Paul |
| 7,147,652 B2 | 12/2006 | Bonutti |
| 7,147,665 B1 | 12/2006 | Bryan et al. |
| 7,153,325 B2 | 12/2006 | Kim et al. |
| 7,172,627 B2 | 2/2007 | Fiere et al. |
| 7,208,013 B1 | 4/2007 | Bonutti |
| 7,217,273 B2 | 5/2007 | Bonutti |
| 7,217,290 B2 | 5/2007 | Bonutti |
| 7,232,464 B2 | 6/2007 | Mathieu et al. |
| 7,276,082 B2 | 10/2007 | Zdeblick et al. |
| 7,309,357 B2 | 12/2007 | Kim |
| 7,311,719 B2 | 12/2007 | Bonutti |
| 7,320,708 B1 | 1/2008 | Bernstein |
| 7,329,263 B2 | 2/2008 | Bonutti |
| 7,429,266 B2 | 9/2008 | Bonutti |
| 7,462,200 B2 | 12/2008 | Bonutti |
| 7,481,831 B2 | 1/2009 | Bonutti |
| 7,510,557 B1 | 3/2009 | Bonutti |
| 7,594,931 B2 * | 9/2009 | Louis ................... A61F 2/4455 606/247 |
| 7,615,054 B1 | 11/2009 | Bonutti |
| 7,618,456 B2 | 11/2009 | Mathieu et al. |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,771,475 B2 | 8/2010 | Michelson |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,846,207 B2 | 12/2010 | Lechmann et al. |
| 7,854,750 B2 | 12/2010 | Bonutti |
| 7,862,616 B2 | 1/2011 | Lechmann et al. |
| 7,875,076 B2 | 1/2011 | Mathieu et al. |
| 7,879,072 B2 | 2/2011 | Bonutti |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 8,100,976 B2 | 1/2012 | Bray et al. |
| 8,128,669 B2 | 3/2012 | Bonutti |
| 8,133,229 B1 | 3/2012 | Bonutti |
| 8,162,977 B2 | 4/2012 | Bonutti |
| 8,343,222 B2 | 1/2013 | Cope |
| 8,425,522 B2 | 4/2013 | Bonutti |
| 8,460,388 B2 * | 6/2013 | Kirwan ................. A61F 2/4611 623/17.11 |
| 8,486,066 B2 | 7/2013 | Bonutti |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 8,739,797 B2 | 6/2014 | Bonutti |
| 8,747,439 B2 | 6/2014 | Bonutti |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,956,417 B2 | 2/2015 | Bonutti |
| 9,044,322 B2 | 6/2015 | Bonutti |
| 9,044,341 B2 | 6/2015 | Bonutti |
| 9,050,152 B2 | 6/2015 | Bonutti |
| 9,364,342 B2 * | 6/2016 | Walkenhorst ....... A61B 17/7059 |
| 2001/0023371 A1 | 9/2001 | Bonutti |
| 2002/0010511 A1 | 1/2002 | Michelson |
| 2002/0016595 A1 | 2/2002 | Michelson |
| 2002/0029055 A1 | 3/2002 | Bonutti |
| 2002/0040246 A1 | 4/2002 | Bonutti |
| 2002/0095160 A1 | 7/2002 | Bonutti |
| 2002/0099444 A1 * | 7/2002 | Boyd .................... A61F 2/4455 623/23.76 |
| 2003/0009147 A1 | 1/2003 | Bonutti |
| 2003/0023260 A1 | 1/2003 | Bonutti |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2004/0010287 A1 | 1/2004 | Bonutti |
| 2004/0078078 A1 | 4/2004 | Shepard |
| 2004/0097794 A1 | 5/2004 | Bonutti |
| 2004/0098016 A1 | 5/2004 | Bonutti |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0143332 A1 | 7/2004 | Krueger et al. |
| 2004/0162618 A1 * | 8/2004 | Mujwid ................. A61F 2/447 623/17.11 |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0230223 A1 | 11/2004 | Bonutti |
| 2004/0254644 A1 * | 12/2004 | Taylor ................... A61F 2/4425 623/17.13 |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0216059 A1 | 9/2005 | Bonutti |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2005/0267534 A1 | 12/2005 | Bonutti |
| 2006/0030851 A1 * | 2/2006 | Bray .................... A61F 2/4455 606/279 |
| 2006/0085071 A1 | 4/2006 | Lechmann et al. |
| 2006/0129240 A1 | 6/2006 | Lessar et al. |
| 2006/0167495 A1 | 7/2006 | Bonutti |
| 2006/0217809 A1 | 9/2006 | Albert et al. |
| 2006/0235470 A1 | 10/2006 | Bonutti |
| 2006/0265009 A1 | 11/2006 | Bonutti |
| 2007/0088441 A1 | 4/2007 | Duggal et al. |
| 2007/0123987 A1 * | 5/2007 | Bernstein ................. A61F 2/44 623/17.11 |

(56) References Cited

U.S. PATENT DOCUMENTS

| | | |
|---|---|---|
| 2007/0123989 A1* | 5/2007 | Gfeller ............... A61B 17/7079 623/17.16 |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0208378 A1 | 9/2007 | Bonutti |
| 2007/0225806 A1 | 9/2007 | Squires et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0270961 A1 | 11/2007 | Ferguson |
| 2007/0270968 A1 | 11/2007 | Baynham |
| 2008/0015694 A1 | 1/2008 | Tribus |
| 2008/0033440 A1* | 2/2008 | Moskowitz ............ A61B 17/92 606/251 |
| 2008/0039873 A1 | 2/2008 | Bonutti |
| 2008/0047567 A1 | 2/2008 | Bonutti |
| 2008/0051890 A1 | 2/2008 | Waugh et al. |
| 2008/0051907 A1 | 2/2008 | Marik |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0133013 A1 | 6/2008 | Duggal et al. |
| 2008/0140011 A1 | 6/2008 | Bonutti |
| 2008/0140117 A1 | 6/2008 | Bonutti |
| 2008/0319481 A1 | 12/2008 | Moore |
| 2009/0076608 A1 | 3/2009 | Gordon et al. |
| 2009/0182430 A1* | 7/2009 | Tyber ................... A61F 2/4465 606/301 |
| 2009/0210062 A1 | 8/2009 | Thalgott et al. |
| 2010/0312346 A1* | 12/2010 | Kueenzi ................ A61F 2/44 623/17.16 |
| 2012/0010623 A1 | 1/2012 | Bonutti |
| 2012/0071978 A1* | 3/2012 | Suedkamp ............ A61B 17/86 623/17.16 |
| 2012/0179259 A1* | 7/2012 | McDonough ......... A61F 2/4611 623/17.16 |
| 2012/0215226 A1 | 8/2012 | Bonutti |
| 2012/0215233 A1 | 8/2012 | Bonutti |
| 2012/0221017 A1 | 8/2012 | Bonutti |
| 2012/0277873 A1* | 11/2012 | Kana ..................... A61F 2/447 623/17.16 |
| 2013/0226185 A1 | 8/2013 | Bonutti |
| 2013/0237989 A1 | 9/2013 | Bonutti |
| 2013/0289729 A1 | 10/2013 | Bonutti |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |
| 2014/0228963 A1 | 8/2014 | Bonutti |
| 2014/0257380 A1 | 9/2014 | Bonutti |
| 2014/0343573 A1 | 11/2014 | Bonutti |

FOREIGN PATENT DOCUMENTS

| | | |
|---|---|---|
| WO | 1997023175 A1 | 7/1997 |
| WO | 1999063914 A1 | 12/1999 |
| WO | 2004071315 A1 | 8/2004 |
| WO | 2005007040 A1 | 1/2005 |
| WO | 2007098288 A2 | 8/2007 |
| WO | 2008014258 A2 | 1/2008 |
| WO | 2011037484 A1 | 3/2011 |

OTHER PUBLICATIONS

U.S. Appl. No. 60/777,663, filed Feb. 27, 2006, Messerli.
U.S. Appl. No. 60/777,732, filed Feb. 27, 2006, Messerli et al.
U.S. Appl. No. 60/838,229, filed Aug. 16, 2006, Hunziker et al.
Guidance Document: Intervertebral Body Fusion Device, U.S. Dept. of Health and Human Services, Food and Drug Administration (Jun. 12, 2007).
M. Spruit et al., The in vitro stabilizing effect of polyetheretherketone cages versus a titanium cage of similar design for anterior lumbar interbody fusion, 14(8) Eur. Spine J. 752, 752-758 (2005).
P. Schleicher et al., Biomechanical comparison of two different concepts for stand alone anterior lumbar interbody fusion, 17(12) Eur. Spine J. 1757, 1757-1765 (2008).
P.W. Pavlov et al., Anterior lumbar interbody fusion with threaded fusion cages and autologous bone grafts, 9 Eur. Spine J. 224, 224-229 (2000).
Synthes' SynFix Technique Guide device ("SynFix Technique Guide").

* cited by examiner

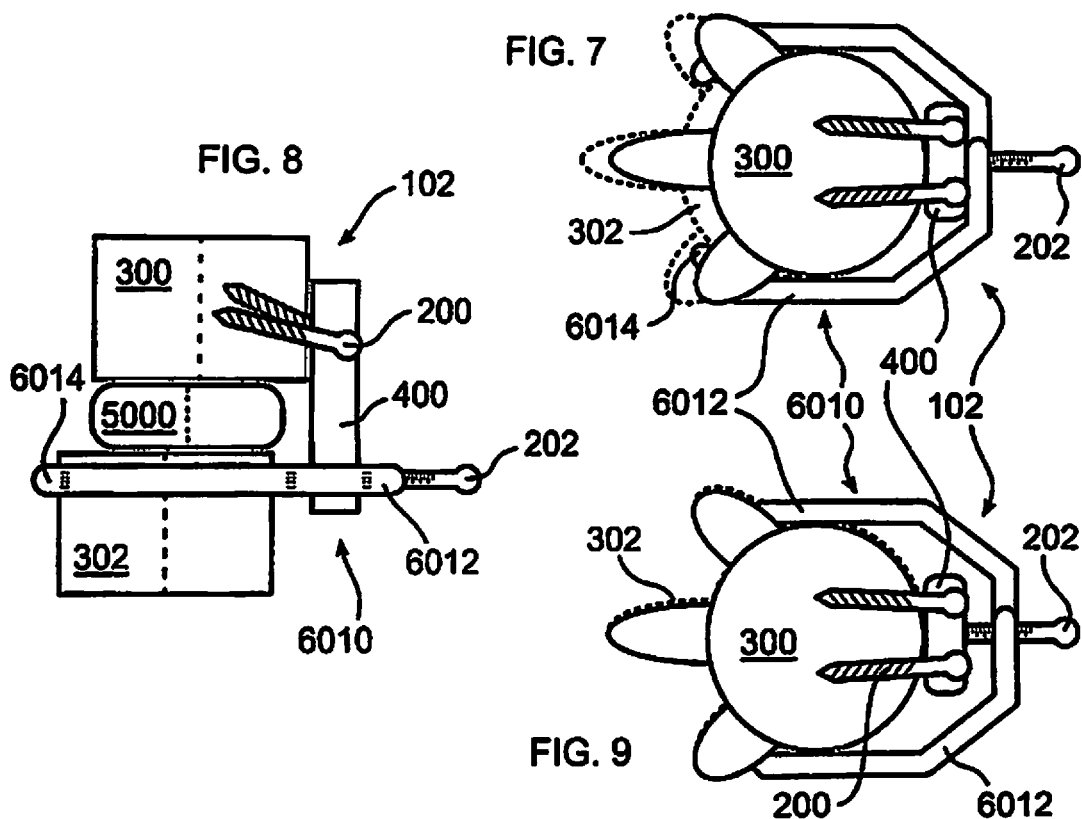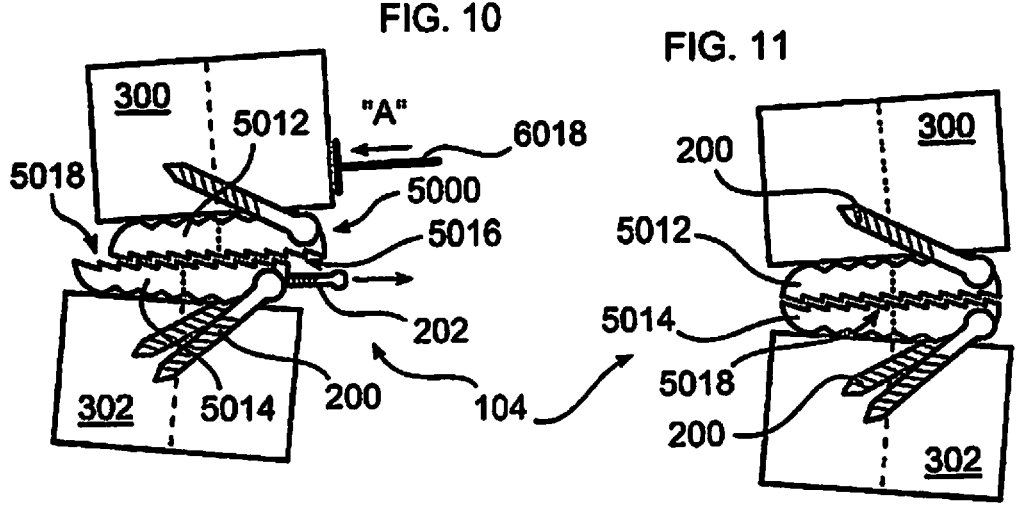

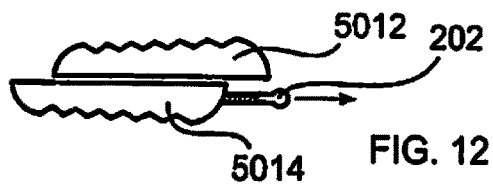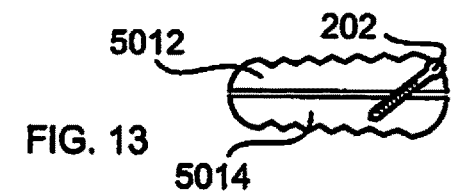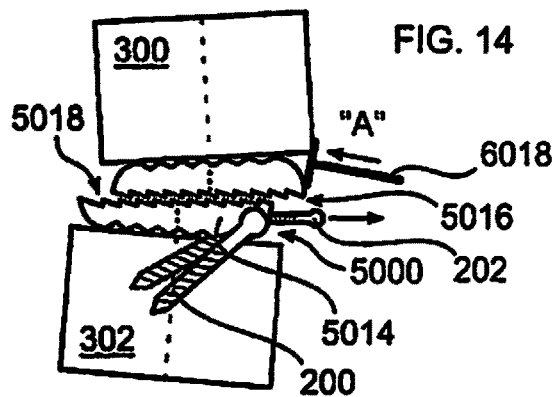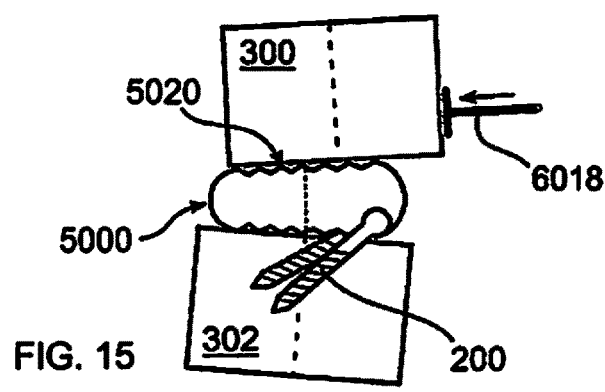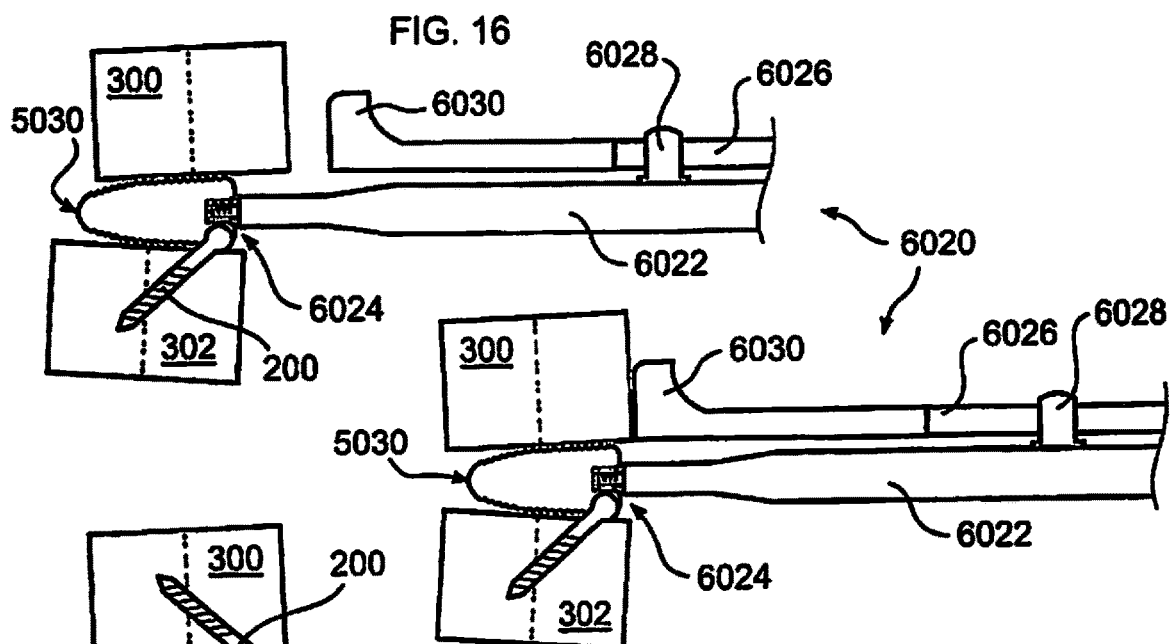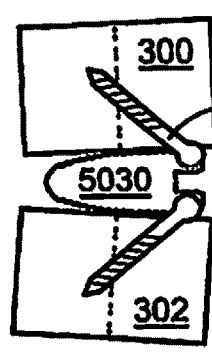

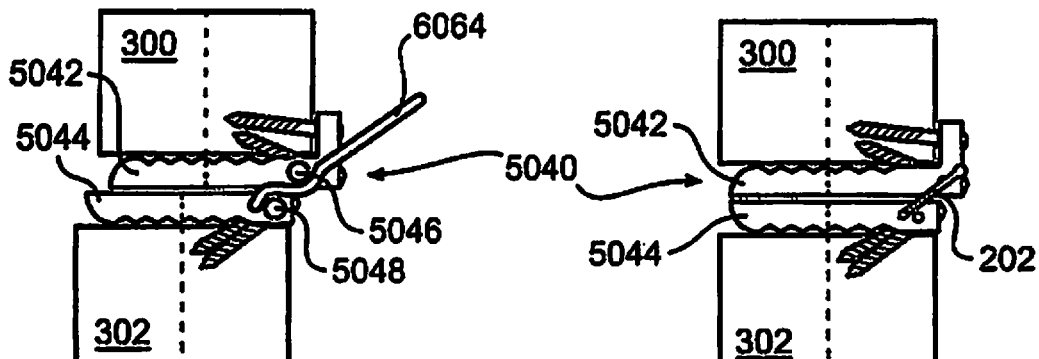
FIG. 22  FIG. 23
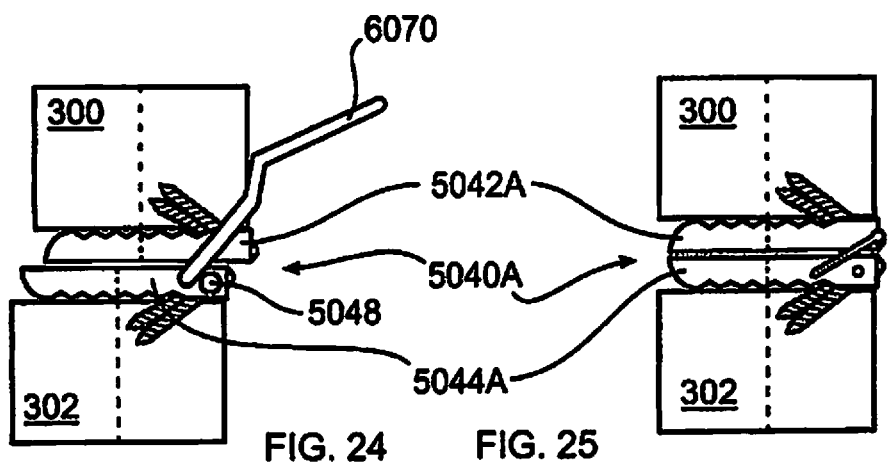
FIG. 24  FIG. 25
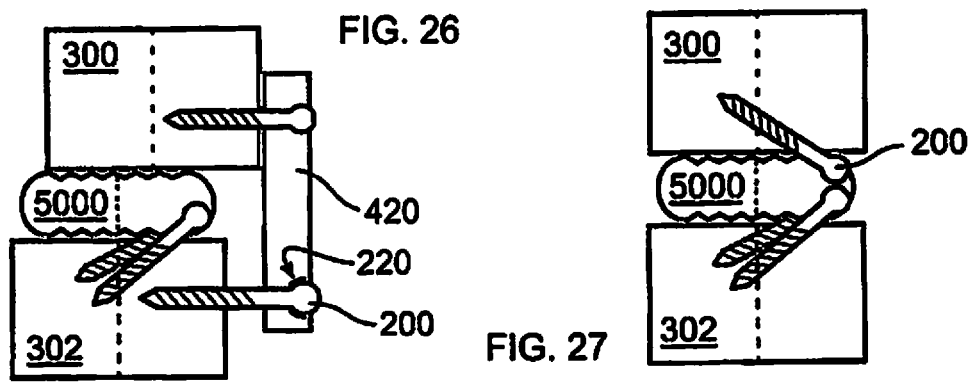
FIG. 26
FIG. 27

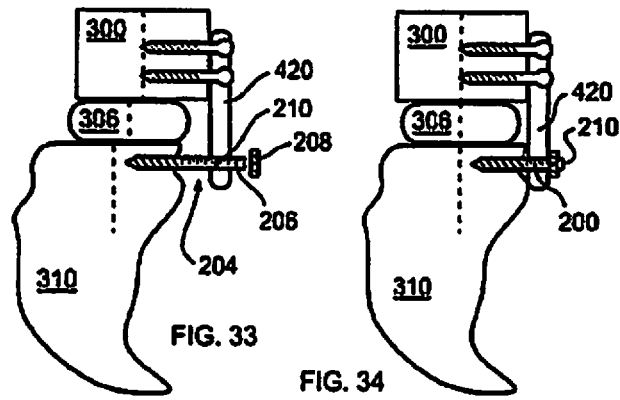
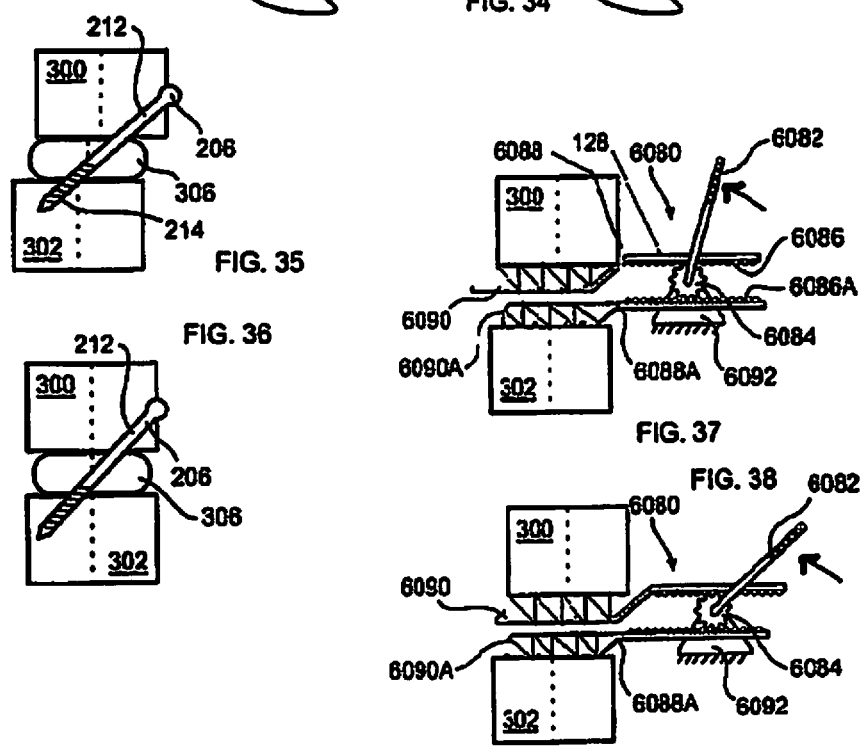

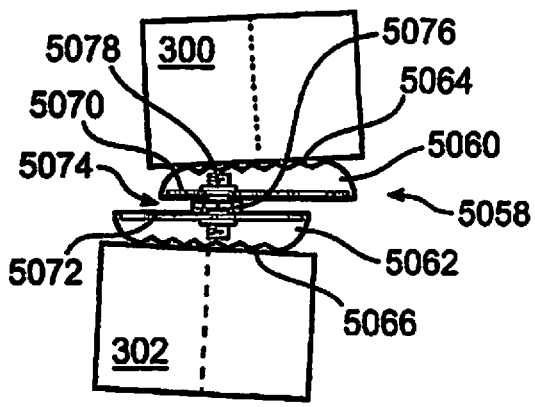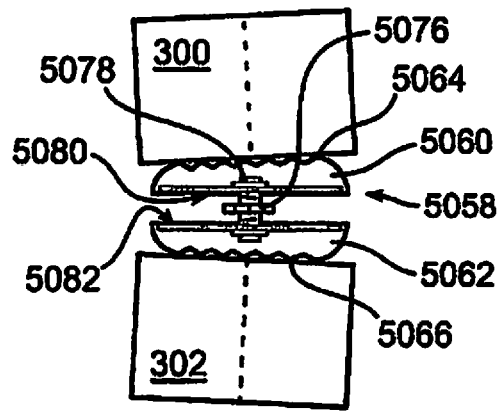
FIG. 39　　　FIG. 40
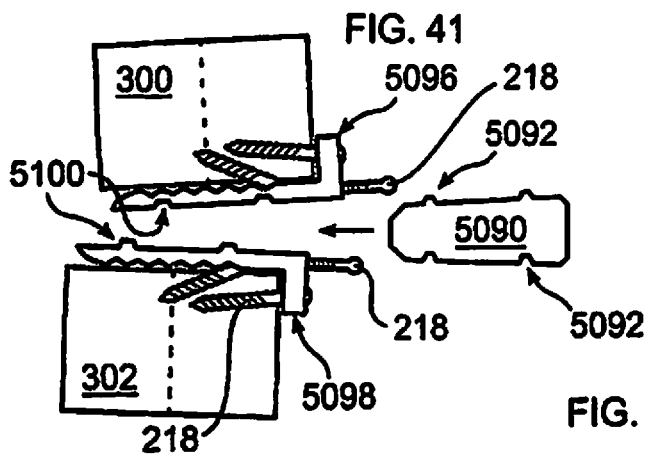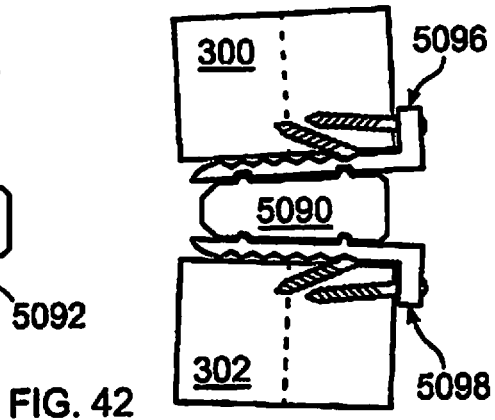
FIG. 41　　　FIG. 42
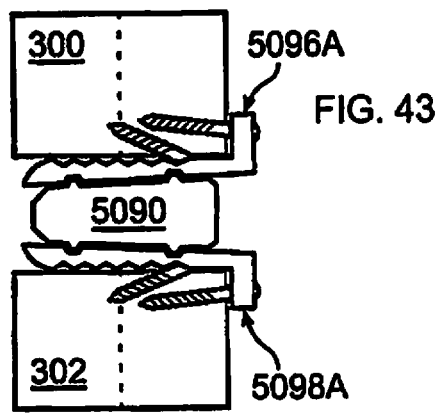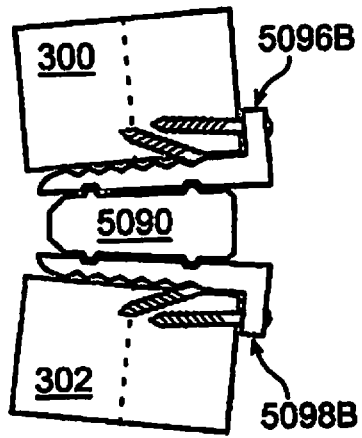
FIG. 43　　　FIG. 44

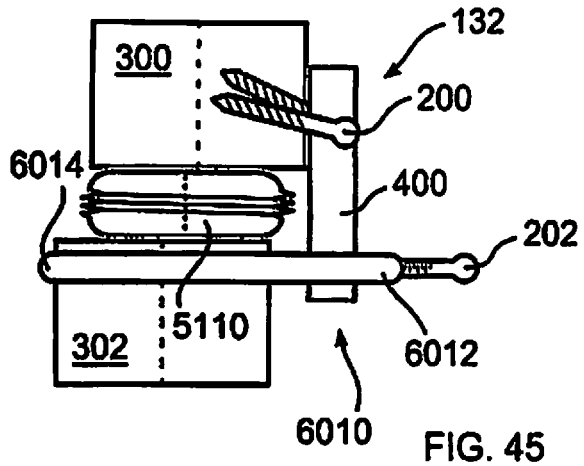
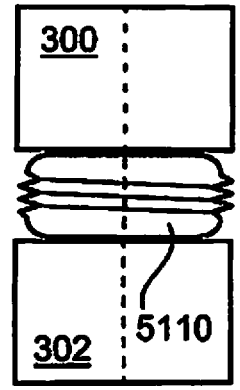
FIG. 45  FIG. 46
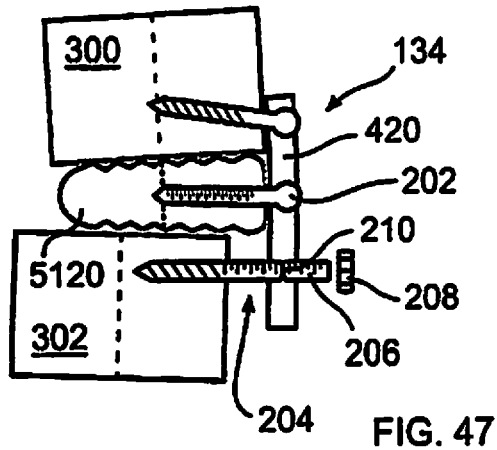
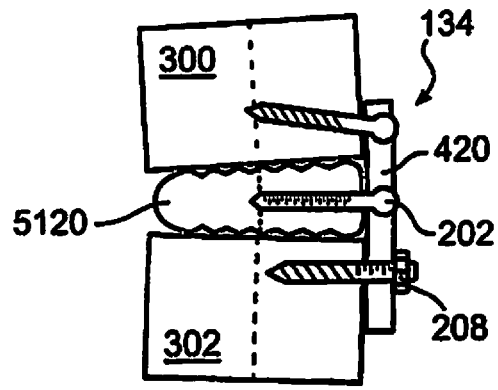
FIG. 47  FIG. 48
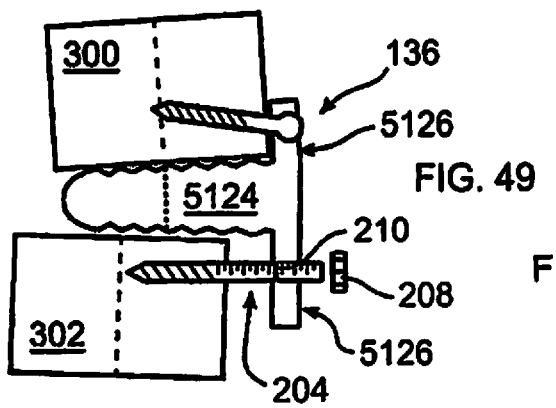
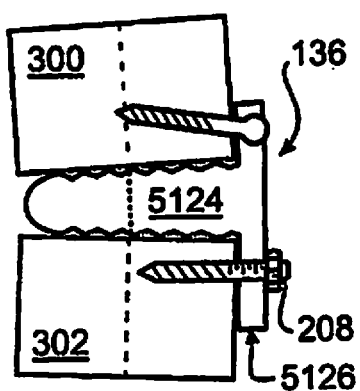
FIG. 49  FIG. 50

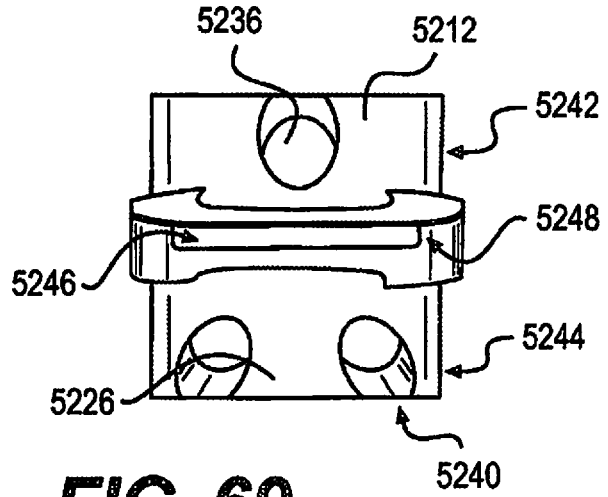
FIG. 69
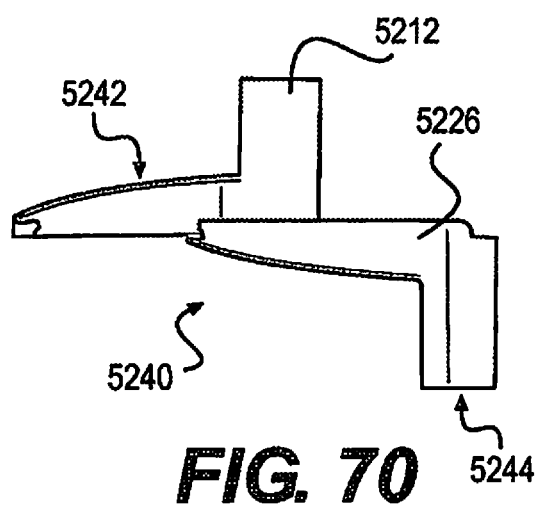
FIG. 70
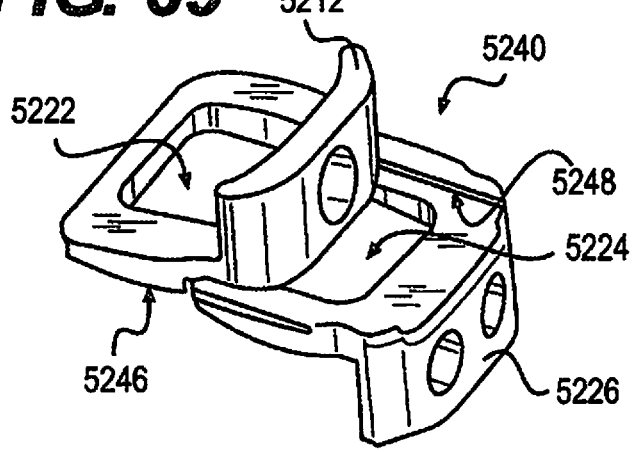
FIG. 71
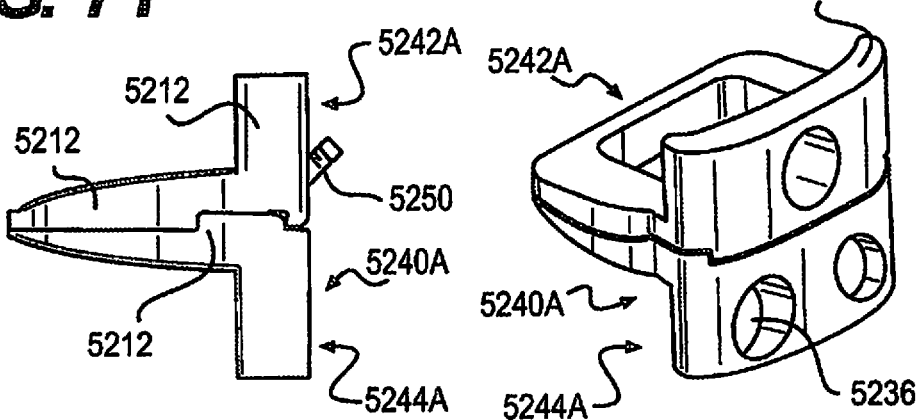
FIG. 72
FIG. 73

ALIGNING VERTEBRAL BODIES

CROSS REFERENCE TO RELATED APPLICATIONS

This Patent Application is a continuation of U.S. patent application Ser. No. 16/739,424, filed on Jan. 10, 2020 (published as U.S. 2020-0214753), which is a continuation of U.S. patent application Ser. No. 13/483,558, filed May 30, 2012 (abandoned), all of which are incorporated by reference herein in their entireties for all purposes.

FIELD OF THE INVENTION

The invention relates to aligning bones of the body, and more particularly to reducing adjacent vertebrae and realigning the vertebral column, for example to correct spondylolisthesis.

BACKGROUND

Bones, bony structures and tissue are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

In some cases, an anterior or posterior displacement of a vertebra with respect to an adjacent vertebra takes place, giving rise to a disorder termed spondylolisthesis. Resultant pressure on nerves can produce pain, stiffening of the back, changes in gait, and muscular atrophy, for example.

Conservative approaches may include physical therapy and treatment with NSAIDs such as acetaminophen. Spinal decompression through, for example, laminectomy or non-surgical methods may be employed. Additionally, a fusion may be carried out, for example a posterolateral fusion of adjacent vertebrae.

SUMMARY

In accordance with the disclosure, a device for therapeutically aligning two misaligned vertebral bodies on opposite sides of a joint, comprises a first rigid extension securable to a first of the misaligned bones using a single approach selected from the group consisting of left lateral approach, right lateral approach, anterior approach, and posterior approach; a second rigid extension having a contacting surface positionable in contact with the second of the two misaligned bones from the approach selected for securing the first rigid extension, the second rigid extension moveable with respect to the first rigid extension when the first rigid extension is secured to the first of the misaligned bones and the second rigid extension is positioned in contact with the second of the two misaligned bones; and a lever configured to lever the first rigid extension with respect to the second rigid extension to move the first rigid extension with respect to the second rigid extension, to thereby exert a pulling force on the first of the two misaligned bones, and a pushing force on the second of the two misaligned bones, aligning the first and second misaligned bones.

In embodiments thereof, the first and second misaligned bones are vertebrae; the device further includes an intervertebral spacer, the first rigid extension securable to the intervertebral spacer, the intervertebral spacer connected to the first of the misaligned bones; and the intervertebral spacer is formed in two segments, each segment attachable to one of the first or second misaligned bones, the segments moveable with respect to each other when attached to a respective misaligned bone.

In other embodiments thereof, the segments moveable in ratcheting engagement with respect to each other; the lever applies leverage using a rotatable thread; the first rigid extension is securable to the misaligned bone using a threaded fastener; the first rigid extension is a plate; the plate forms a levered connection between the first and second misaligned bones; the first rigid extension extends around the first misaligned bone to contact a portion of the first misaligned bone which faces an approach different from the approach selected; and one of the first or second misaligned bones is the sacrum.

In yet further embodiments thereof, the lever is a screw having threads configured to engage bone on a first end, and threads configured to engage a nut on a second, opposite end, the nut rotated about the second end moves the second rigid extension and to thereby lever the first and second misaligned bones into alignment; the device further includes an intervertebral spacer; and the intervertebral spacer is expandable to increase a distance between the first and second misaligned bones.

In another embodiment of the disclosure, a device for therapeutically aligning two vertebrae, comprises a first rigid extension securable to a first of the vertebrae using a single approach selected from the group consisting of left lateral approach, right lateral approach, anterior approach, and posterior approach; a second rigid extension having a contacting surface positionable in contact with the second of the two vertebrae from the approach selected for securing the first rigid extension, the second rigid extension moveable with respect to the first rigid extension when the first rigid extension is secured to the first of the vertebrae and the second rigid extension is positioned in contact with the second of the two vertebrae; a lever configured to lever the first rigid extension with respect to the second rigid extension to move the first rigid extension with respect to the second rigid extension, to thereby exert a pulling force on the first of the two vertebrae, and a pushing force on the second of the two vertebrae, aligning the first and second vertebrae; and a fastener configured to maintain the first and second vertebrae in relative alignment.

In embodiments thereof, the device further includes an intervertebral spacer connectable to at least one of the first and second rigid extensions during alignment of the vertebrae, and connectable to both vertebrae to maintain the vertebrae in relative alignment; and the first rigid extension forming a first portion of an intervertebral spacer, the second rigid extension forming a second portion of an intervertebral spacer, the first and second portions mateably engageable and maintainable in relative mutual engagement using a ratchet.

In a further embodiment of the disclosure, a method for therapeutically aligning two misaligned bones on opposite sides of a joint, comprises securing a first rigid extension to a first of the misaligned bones using a single approach selected from the group consisting of left lateral approach, right lateral approach, anterior approach, and posterior approach; contacting the second of the misaligned bones with a second rigid extension, the second rigid extension having a contacting surface positionable in contact with the second of the two misaligned bones from the approach selected for securing the first rigid extension, the second rigid extension moveable with respect to the first rigid extension when the first rigid extension is secured to the first of the misaligned bones and the second rigid extension is positioned in contact with the second of the two misaligned bones; and levering the first rigid extension with respect to the second rigid extension using a lever configured to move the first rigid extension with respect to the second rigid extension, to thereby exert a pulling force on the first of the two misaligned bones, and a pushing force on the second of the two misaligned bones, aligning the first and second misaligned bones.

In embodiments thereof, the method further includes inserting an intervertebral spacer between the two misaligned bones; and further includes connecting the intervertebral spacer to the first of the misaligned bones; and applying the lever between the intervertebral spacer and the second of the misaligned bones.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 7 is a diagram of the joint of FIG. 1, and a top view of a reaching tool and plate of the disclosure;

FIG. 8 depicts the joint and device of FIG. 7, in a cross-section;

FIG. 9 depicts the joint and device of FIG. 8, the joint aligned using the device of FIG. 8;

FIG. 10 is a diagram of the joint of FIG. 1, and a cross-section of spacer of the disclosure having two ratcheting segments;

FIG. 11 depicts the joint and device of FIG. 10, the joint aligned by the device of FIG. 10;

FIG. 12 is a cross-section of a segmented spacer of the disclosure;

FIG. 13 depicts the spacer of FIG. 12, the segments mutually secured by a fastener;

FIG. 14 is a diagram of the joint of FIG. 1, a cross-section of a ratcheting spacer of the disclosure, and an indication of an application of a force to align the joint;

FIG. 15 is a diagram of the joint of FIG. 1, and a spacer of the disclosure, and an indication of an application of a force to align the joint;

FIG. 16 is a diagram of the joint of FIG. 1, and a cross-section of a spacer and tool in accordance with the disclosure;

FIG. 17 depicts the joint and device of FIG. 16, the device having aligned the joint;

FIG. 18 depicts the joint and spacer of FIG. 17, the spacer secured to the aligned joint;

FIG. 22 is a diagram of the joint of FIG. 1, and a segmented spacer and lever of the disclosure;

FIG. 23 is a diagram of the joint and device of FIG. 22, the joint having been aligned by applying the lever to the device;

FIG. 24 depicts the joint and device of FIG. 23, the joint having been aligned by applying the lever to a segment and to the joint;

FIG. 25 depicts the joint and device of FIG. 24, the segments joined by a fastener;

FIG. 26 is a diagram of the joint of FIG. 1, and a cross-section of a spacer and plate of the disclosure;

FIG. 27 depicts the joint and spacer of FIG. 26, the joint having been aligned by the plate, and the spacer secured to both sides of the joint using fasteners;

FIG. 33 is a diagram of the joint of FIG. 31, and a cross-section of a plate and fastener of the disclosure;

FIG. 34 depicts the joint and device of FIG. 33, the joint having been aligned by the device, the fastener shortened after use;

FIG. 35 is a diagram of the joint of FIG. 1, and a fastener of the disclosure;

FIG. 36 depicts the joint and fastener of FIG. 35, the joint having been aligned by the fastener;

FIG. 37 is a diagram of the joint of FIG. 1, and a ratcheting device of the disclosure connected to each side of the joint;

FIG. 38 depicts the joint and device of FIG. 37, the joint having been aligned by the device;

FIG. 39 is a diagram of the joint of FIG. 1, and a cross-section of a segmented spacer of the disclosure;

FIG. 40 depicts the joint and spacer of FIG. 39, the joint secured in alignment, and distracted, using the device of FIG. 39;

FIG. 41 is a diagram of the joint of FIG. 1, and a cross-section of a segmented spacer having three mateable portions, including opposed segments and a wedge shaped spacer;

FIG. 42 depicts the joint and device of FIG. 41, the spacer having been inserted between the opposed segments, and the joint, opposed segments, and spacer maintained in alignment by fasteners and a mating engagement between the opposed segments and the spacer;

FIG. 43 depicts the joint and device of FIG. 40, the opposed segments shaped to reduce an angle formed between bones of the joint;

FIG. 44 depicts the joint and device of FIG. 40, the opposed segments shaped to increase an angle formed between bones of the joint;

FIG. 45 depicts a diagram of the joint of FIG. 1, and an expandable spacer, plate, and reaching tool of the disclosure;

FIG. 46 depicts the spacer and device of FIG. 45 in an expanded configuration, distracting bones of the joint, the joint having been aligned by the spacer, plate, and reaching tool;

FIG. 47 is a diagram of the joint of FIG. 1, and a cross-section of a spacer, angled plate, and fastener of the disclosure;

FIG. 48 depicts the joint and device of FIG. 47, the joint having been aligned using the device, the fastener having been shortened after use;

FIG. 49 is a diagram of the joint of FIG. 1, and a cross-section of spacer, integrated plate, and fastener of the disclosure;

FIG. 50 depicts the joint and device of FIG. 49, the joint having been aligned by the device, the fastener shortened after use;

FIG. 69 is a back view of a combined spacer and plate in two segments, the segments slidingly engageable along an A-P axis;

FIG. 70 is a side view of the device of FIG. 69, the segments partially slidingly engaged;

FIG. 71 is a perspective view of the device of FIG. 70;

FIG. 72 is a side view of a combined spacer and plate in two segments, the segments slidingly engageable along a lateral axis;

FIG. 73 is a perspective view of the device of FIG. 72;

DETAILED DESCRIPTION OF THE ILLUSTRATED EMBODIMENTS

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figure 1:
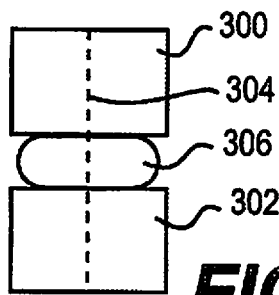
FIG. 1 is a diagram of a joint of a body.
Figure 2:
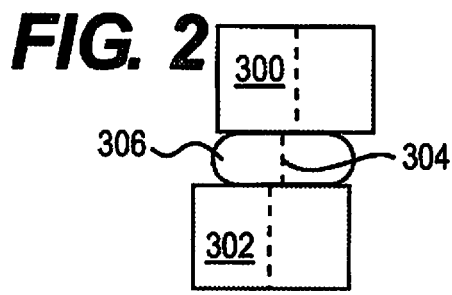
FIG. 2 is a diagram of the joint of FIG. 1, misaligned.

With reference to FIG. 1, a healthy pair of vertebrae 300, 302 are diagrammatically illustrated. Although adjacent vertebrae are not identical in the body, to simplify an understanding of an operation of devices and methods of the disclosure, a centrally disposed dotted line 304 represents a natural overlapping of bones. The disc annulus surrounding the nucleus pulposus is diagrammatically illustrated as disc 306, positioned in alignment with both vertebrae. In FIG. 2, vertebrae 300, 302 are relatively displaced, representing a patient condition addressed by the disclosure, for example degenerative fibrocartilage, malignancy, herniation, protrusion, spondylolysis, spondylolisthesis, spinal stenosis, or degenerative disc disease. While one vertebra 300 appears to be oriented in an upper, or superior location with respect to the other vertebra 302, it should be understood that within the body, superior, inferior, or both bones may be displaced, and that a superior or inferior position of adjacent bones should not be assumed within the disclosure. In addition, a displacement may be anterior, posterior, or lateral.

In the various embodiments described herein, the spine and vertebrae are described as the bones to be aligned. However, it should be understood that the methods and devices of the disclosure are readily applied or adapted to be used with other bones of the body, for example in size and shape. Such other bones include the joints of the fingers, hand, wrist, elbow, shoulder, hip, knee, ankle, foot, or toes. Non-jointed tissue, such as bony plates, for example misaligned after trauma, may also be aligned as described herein. Accordingly, the disclosure should be considered in light of other bones and tissue, throughout.

In various embodiments, the devices and methods of the disclosure provide solutions for treating diseases of the spine, for example, isthmic spondylolisthesis, from a single approach, such as advantageously an anterior approach. This avoids a requirement of an approach through two separate aspects of the body, for example also a posterior approach. This reduces trauma to the patient, recovery time, time to complete the surgical procedure, risk, and cost. While an anterior approach is possible, it should be understood that a lateral or posterior approach is similarly possible, while retaining the advantage of aligning bones of a joint from a single approach, including only one of a left lateral approach, a right lateral approach, an anterior approach, or a posterior approach.

Figure 3:
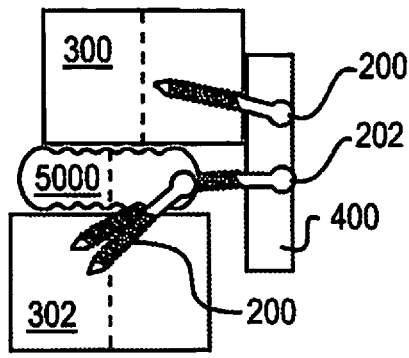
FIG. 3 is a diagram of the joint of FIG. 1, and a cross-section of a connected plate and spacer of the disclosure.

In FIG. 3, an intravertebral spacer 5000 engages one or more fasteners, for example bone screws 200, for example by passing a polyaxial screw through an aperture, not shown, or through some other configuration understood within the art. In this manner, a position of spacer 5000 may become fixed with respect to one or more vertebrae, at least for a sufficient period of time for healing and or fusion between the body and the spacer to take place, for example through bony ingrowth. Spacer 5000 may be provided with spaces, channels, texture, or other structure which encourages bone ingrowth, and may further be provided with therapeutic substances which encourage bone growth.

With further reference to FIG. 3, an assembly in accordance with the disclosure includes a plate 400, fasteners or screws 200, 202, and an intervertebral spacer 5000. Spacer 5000 is secured to a vertebra 300 using one or more bone screws 200 or other fastener. It should be understood that while a bone screw 200 is illustrated in the drawings, for clarity, any fastener suitable for connecting an implant to a bone may be used, including adhesive, as would be understood by one skilled in the art. In this configuration, vertebra 300 is closer to the surgical approach than vertebra 302. For example, in an anterior approach, vertebra 300 is shifted anteriorly with respect to vertebra 302. In a lateral or posterior approach, plate 400 would be applied to the more lateral or posterior vertebra, respectively.

Plate 400, in accordance with this and other embodiments of the disclosure, may have a flat, rectangular or bar shape such as is illustrated in the drawings, for clarity, or may be contoured and or curved, or shaped to closely conform, to the body tissue to which it is attached. In some embodiments, the plate 400 is rigid, while in other embodiments, the plate 400 can be flexible or bendable. In some embodiments, the plate 400 is configured such that in an unstressed state, the plate 400 is flat, while in a stressed state, it is curved.

Figure 4:
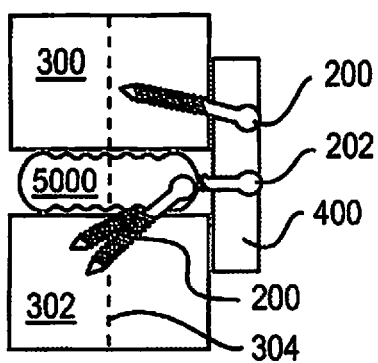
FIG. 4 depicts the joint of FIG. 1, aligned using the plate and spacer of FIG. 3.

After plate 400 is secured to vertebra 300, a screw 202 or other fastener configured to perform a like function, is connected between plate 400 and spacer 5000. Screw 202 is rotatably connected to plate 400 whereby as screw 202 is rotated, spacer 5000 is drawn closer to plate 400. Herein, screws should be considered as levers; accordingly, screw 200 functions as a lever to facilitate movement of one vertebra with respect to another. Vertebra 302, being connected to spacer 5000, is likewise drawn closer to plate 400 as screw 202 is rotated, the assembly thereof ultimately causing the therapeutically correct disposition of vertebrae 300, 302 shown in FIG. 4. As is the case with this and other embodiments of the disclosure, after correction, the assembly may be permanently left in the body, or may be removed after a therapeutic period of time.

Figure 5A:
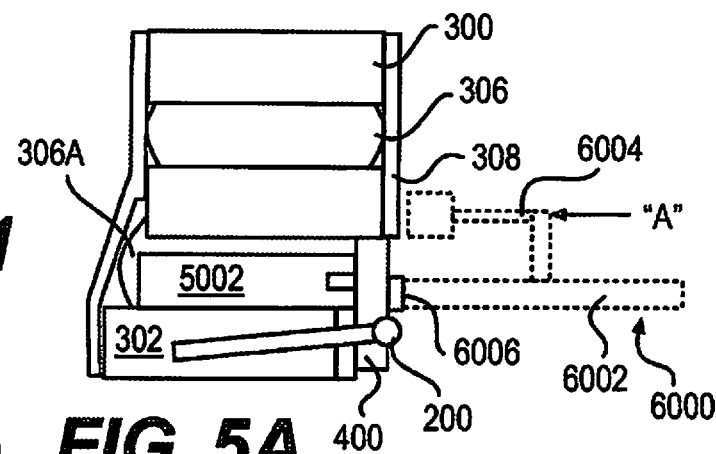
FIG. 5A depicts the joint of FIG. 1, and a cross section of a spacer, plate, and tool of the disclosure
Figure 5B:
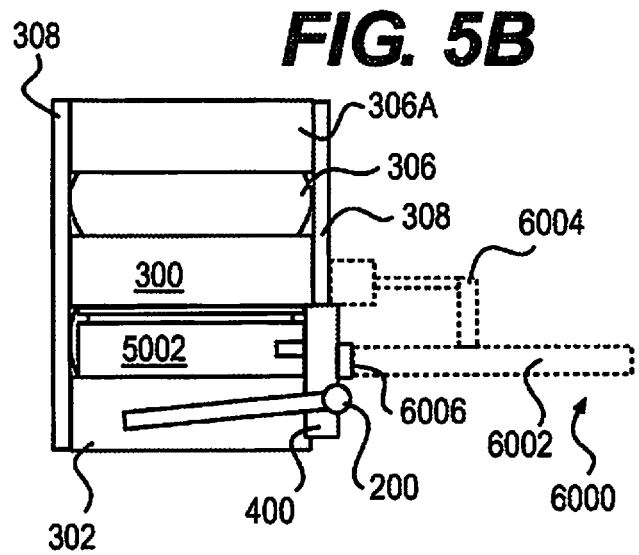
FIG. 5B is a diagram of the joint of FIG. 1, the joint having been aligned using the spacer, plate, and tool of FIG. 5A.
Figure 6:
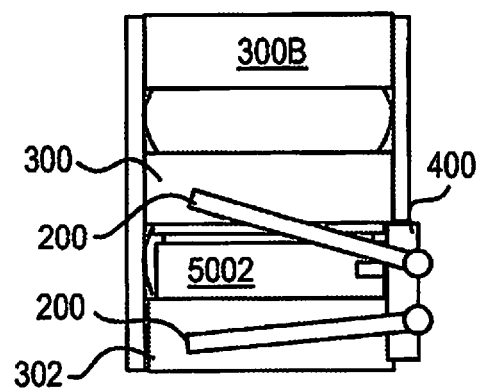
FIG. 6 is a diagram of the joint of FIG. 1, and the spacer and plate of FIG. 5B secured to the joint using fasteners, from a cross-section.

Referring now to FIGS. 5A, 5B, and 6, vertebrae 300 and 302, as well as associated ligaments 308, are relatively displaced. In this embodiment, an expanding spacer 5002 is positioned between vertebrae 300, 302, for example after removal of all or part of intervertebral tissue, or disc 306A. In this illustration, an additional vertebral level is shown, including vertebra 300A. It should be understood in all embodiments herein that more than one level may be corrected using methods and devices of the disclosure. For example, multiple plates may be used, or longer plates spanning more than one level.

In FIGS. 5A, 5B, and 6, spacer 5002 may be of any known or hereinafter invented type, including spacers having, for example, mechanical or hydraulic mechanisms of expansion. Vertebra 302 is connected to plate 400 with bone screw 200. In one embodiment, spacer 5002 is connected to plate 400, to ensure that spacer 5002 remains in position with respect to vertebra 302, although this is not needed in all cases. For example, spacer 5002 may be separately engaged with vertebra 302. Tool 6000 includes a brace 6002 and a driver 6004 moveably connected to brace 6000. Brace 6000 is releasably engageable with plate 400 at connector 6006.

To correct an alignment of the spine, driver 6004 is moved with respect to brace 6002, for example through a threaded, hydraulic, motor, or other moveable attachment between driver 6004 and brace 6002. It should be understood that herein, drawings are not necessarily to scale, and that portions of spacers, plates, their assemblies, or insertion and reduction tools may be sized to be inserted in their entirety, or as portions to be assembled, through a minimally invasive incision or through one or more percutaneous punctures, for example using an endoscope or cannula. As brace 6002 is connected with plate 400, a movement in the direction of arrow "A" in FIG. 5A causes a displacement in the direction "A" of vertebra 300 and associated ligaments 308. Prior to, during, or after movement of vertebra 300, spacer 5002 may be expanded to dispose vertebrae 300, 302 at a correct relative distance, and to provide further stability to the spine. In FIG. 6, tool 6000 is detached, and if needed, an additional bone screw 200 may connect plate 400 and vertebra 300. One or more screws 200 may alternatively pass through plate 400, spacer 5002, and or vertebra 300. In an alternative embodiment, plate 400 is not used, and brace 6002 is releasably connectable to expanding spacer 5002.

With reference to FIGS. 7-9, an assembly of the disclosure includes a tool 6010 cooperative with plate 400, attached to vertebra 300 by screws 200. Tool 6010 includes a chassis 6012 extendable around a vertebra, and moveably attached to plate 400. In some embodiments, the chassis 6012 can be formed of multiple pieces, or of a single piece. More particularly, plate 400 attaches to a first vertebra 300, extends proximate a second vertebra 302 which it is desired to reduce into alignment with the first vertebra 300. Chassis 6012 includes one or more extensions attached to plate 400, extending to engage vertebra 302 about a side of vertebra 302 opposite to a location of plate 400, to thereby at least partially encircle vertebra 302 to effect a positive engagement. It should be understood, however, that chassis 6012 may frictionally engage vertebra 302 along a side surface of vertebra 302, or may be connected to vertebra 302 with one or more fasteners.

In the embodiment shown, screw 202 threadably engages chassis 6012 and rotatably contacts plate 400, whereby as screw 202 is turned, chassis 6012 is pushed away from plate 400, thereby drawing vertebra 302 into alignment with vertebra 300. When a desired alignment is accomplished, vertebra 302 may be attached to plate 400 to maintain the alignment, or vertebra 302 may be fastened to spacer 5000, or to vertebra 300, by any other known or hereinafter invented means, if needed. Once vertebra 302 is sufficiently stable in its new disposition, tool 6010 may be removed.

In FIGS. 10 and 11, an assembly of the disclosure includes a spacer 5010 which is formed of two mating portions 5012, 5014, and forms, in the illustrated embodiment, an angular external profile corresponding to a desired disposition of adjacent vertebrae 300, 302. It should be understood that the illustrated concept applies equally to non-angular or other external profiles. Mating portions 5012, 5014 are provided with serrations, teeth, or other interlocking engagements 5016, 5018, whereby when mating portions 5012, 5014 are overlapped completely or to a desired extent, a relative position of mating portions 5012, 5014 is fostered, particularly when mating portions 5012, 5014 are pressed together, for example between vertebrae 300, 302, by natural compression and associated ligaments 308 (not shown). Mating portions 5012, 5014 may also be secured together by a fastener, including a screw or adhesive.

In FIGS. 10-11, interlocking engagements 5016, 5018 have the form of ramped teeth, whereby a mutual sliding engagement, advantageously in a direction of therapeutic alignment of vertebrae 300, 302, is facilitated, but discouraged in a direction away from therapeutic alignment, as may be seen in FIGS. 10-11. A tool 6018, diagrammatically illustrated in FIG. 10, urges, translates, or pushes the vertebra 300 in a desired direction indicated by arrow "A". Tool 6018 may be a mechanical device, for example as described within this disclosure, or may be a medical practitioner's hand.

In an embodiment illustrated in FIGS. 12-13, mating portions 5012, 5014 may or may not have interlocking engagements, as shown, but are secured in mutual engagement by a fastener, such as screw 202, which is advantageously the same screw as used to manipulate mating segment 5014 in FIG. 10. Screw 202 may advantageously be passed through a first vertebra 300 and threadably fastened into a second vertebra 302.

Tool 6018, diagrammatically illustrated in FIG. 14, may be configured and or used to engage both spacer 5000 and vertebra 300, advancing both together until a therapeutic alignment is attained. After reduction, vertebrae 300, 302 and spacer 5000 may be secured as described elsewhere within the disclosure.

In FIG. 15, vertebra 300 is reduced in sliding engagement with spacer 5000. After reduction, natural or induced compression, for example by compression due to body weight, or engagement with bone screws, promotes insertion of textured surface or projections 5020 with bone or body tissue, securing a position of spacer 5000 and relative alignment of vertebrae 300, 302.

In FIG. 16, an assembly of the disclosure includes instrument or tool 6020, used to reduce vertebra 300 in cooperation with spacer 5030. A brace 6022 abuts or connects with spacer 5030, which may be adapted to securely engage brace 6022 during reduction. In the example of FIGS. 16-18, a threaded connection 6024 is used, although other types of releasable mechanical abutments or interlocks may be used. Once brace 6022 is connected with spacer 5030, it may serve to align and guide a push rod 6026, slideably connected to brace 6022 by a guide 6028, in this embodiment a guide ring attached to brace 6022 through which push rod 6026 slideably passes. An engagement surface 6030 is sized and shaped to move within the body, securely contact body tissue, and urge bones into alignment when push rod 6026 is pushed towards body tissue. Once vertebrae 300, 302 are aligned, tool 6020 may be disconnected from spacer 5030 and removed from the body. In one embodiment, tool 6020 is sized and dimensioned to be used through a minimally invasive percutaneous opening in the skin, or using endoscopic techniques.

Figure 19:
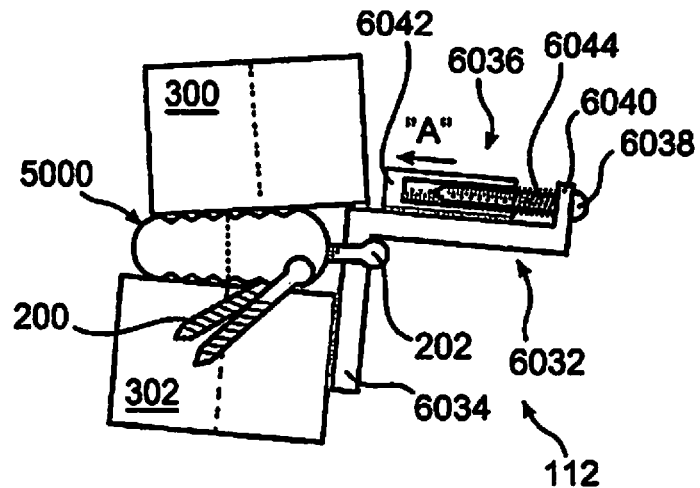
FIG. 19 is a diagram of the joint of FIG. 1, and a cross-section of a spacer and tool of the disclosure.

As with the embodiment of FIGS. 16-18, the assembly of FIG. 19 engages a tool to a spacer, to anchor and orient a tool for displacing and realigning a bone. In the embodiment of FIG. 19, tool 6032 is releasably connected to spacer 5000, in this embodiment with screw 202, and includes a lever 6034 which transmits a displacement force to an adjacent vertebra 302. A threaded adjuster 6036 includes a screw 6038 rotatably mounted to a guide 6040, screw 6038 operative to advance an engagement surface 6042 to contact and move vertebra 300. As resistance is imparted to tool 6032, force is transferred to screw 202, and a rotational moment of tool 6032 is transferred to lever 6034. In this manner, the vertebrae 300, 302 to be relatively aligned share a load force, and are each displaced to an extent, in opposite directions. This is further advantageous at least for the reasons that the tool is stabilized, and a displacement force imparted by tool 6032 is shared between spacer 5000 and vertebra 302. In some embodiments, a biasing member, such as for example an optional spring 6044, may advantageously be included to bias engagement surface 6042 in a direction of vertebra 300. Additionally or alternatively, the spring 6044 may limit an extent of force imparted to vertebra 300 by screw 202 and engagement surface 6042, by enabling screw 6038 to move in an opposite direction to an applied force against vertebra 300. In other embodiments, the screw 6038 acts on its own without the assistance of a biasing member, such as spring 6044.

Figure 20:
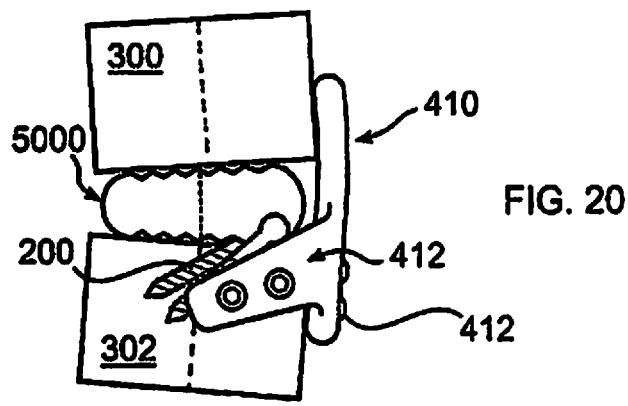
FIG. 20 is a diagram of the joint of FIG. 1, and a reaching plate of the disclosure.

With reference to FIG. 20, an assembly of the disclosure includes a plate 410 which has one or more guide extensions 412 operative to maintain a relative alignment of plate 410 and vertebra 302 as vertebra 300 is reduced. More particularly, one or more screws 412 may be used to draw vertebra 302 towards a conforming engagement with plate 412. Concomitantly, an upper portion 414 of plate 410 contacts vertebra 300, which is displayed in a manner such as is illustrated in FIG. 19. When screws 412 are fully seated, plate 410 is in conforming engagement with vertebra 300 and 302, upper portion 414 having urged vertebra 300 into alignment with vertebra 302, as shown. Guide extensions 412, extending for example on opposing sides of vertebra 302, may be secured to vertebra 302 to maintain a lateral alignment of plate 410 with respect to vertebra 302. Upper portion 414 may be secured to vertebra 300, or as shown, may moveably contact vertebra 300, allowing an extent of natural movement between vertebrae 300, 302.

Figure 21:
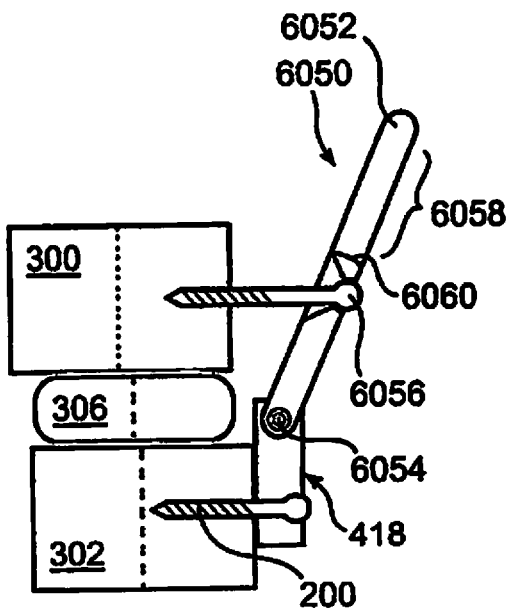
FIG. 21 is a diagram of the joint of FIG. 1, and a hinged plate and lever of the disclosure.

In FIG. 21, an assembly of the disclosure includes tool 6050 having a lever 6052 pivotally connected to plate 418 at hinge 6054. Plate, 418 is connected to vertebra 302 by a fastener, such as one or more screws 200. A lever screw 6056 is moveably connected to lever 6052, and is connected to vertebra 300. As lever 6052 is pivoted, for example by application of a manual or mechanical force, vertebra 300 is moved correspondingly. When a desired alignment of vertebra 300 is attained, tool 6050 and plate 418 may be removed. Alternatively, hinge 6054 may be disassembled, and plate 418 may remain in the body. In such an embodiment, plate 418 may be configured to fuse vertebrae 300, 302, for example by being taller than illustrated, wherein screw 200 may be passed through plate 418 into vertebra 300. In another alternative, screw 6056 may be seated to secure lever 6052 against vertebra 300. An extending portion 6058 of lever 6052, if present, may be removed, for example by disassembly, or by being separated from a remainder of lever 6052 at a weakened portion 6060. In this configuration, articulation is preserved or provided between vertebrae 300 and 302, at hinge 6054.

With reference to FIGS. 22-23, an assembly of the disclosure includes a lever 6064 which engages lever points 5046, 5048, shown as projecting pins on separate portions 5042, 5044 of spacer 5040. Lever 6064 is advantageously sized and shaped to lever vertebrae 300, 302 into a correct relative alignment by applying an opposing force to lever points 5046, 5048. After a therapeutic alignment has been carried out, portions 5042, 5044 of spacer 5040 may be affixed relative to each other by a fastener, for example screw 202, as shown in FIG. 23. Projections 5046, 5048 may be removed after use. Alternatively, it should be understood that lever points 5046, 5048 may be recesses or cutouts formed in portions 5042, 5044, thereby reducing an overall profile of spacer 5040.

FIGS. 24 and 25 are analogous to FIGS. 22-23, however lever 6070 engages one of separate portions 5042A, 5044A, of spacer 5040A, and body tissue associated with an opposed vertebra. Lever 6070 thereby directly pushes body tissue of vertebra 300, obtaining leverage provided by lever point 5048, attached to an adjacent vertebra 302. FIGS. 22-23 and 24-25 illustrate differing forms of spacer, 5040 and 5040A, in order to demonstrate additional advantageous embodiments of spacer. It should be understood that spacers illustrated throughout the specification may be substituted with each other, as would be understood by one skilled in the art.

In FIGS. 26-27, an assembly of the disclosure includes plate 420 which is fastened to vertebra 300, and a screw 200 is rotatably connected to plate 420 and threadably engaged with vertebra 302, whereby progressive rotation of screw 200 draws vertebrae 300, 302 into mutual conforming contact with plate 420. As with all embodiments herein, screw 200 may be any form of bone screw best adapted to the body tissue of the patient and the forces of the application, including for example a Gruberger or lag screw. One or more washers 220, for example polymeric or metallic washers, may additionally be used to avoid damage to an implanted component, or to avoid the production of debris. After the bones are reduced, plate 420 may be removed, as illustrated in FIG. 27, or may remain in the body for a period of time, for example until vertebra 300, 302 are stable in relative relation, or have fused if fusion is desired. In FIG. 27, fasteners such as screws 200 are illustrated, maintaining vertebrae 300, 302 in relative position through engagement with spacer 5000. In the various embodiments, spacer 5000 is illustrated for simplicity and clarity. It should be understood, however, that a position of vertebrae 300, 302 may be maintained by any other known or hereinafter developed method, including for example rods, dynamic fixation, articulating plates, or cables. In embodiments, lever 6064 or lever 6070 has the form of an elongated bar.

Figure 28:
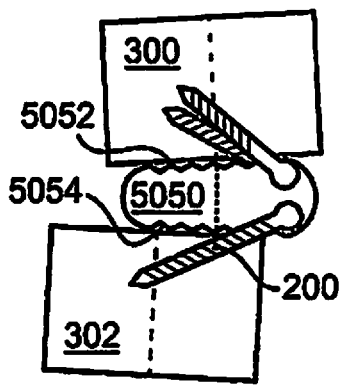
FIG. 28 is a diagram of the joint of FIG. 1, and a spacer of the disclosure.
Figure 29:
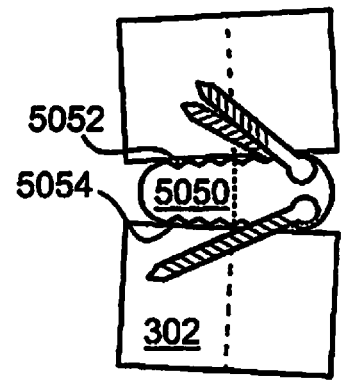
FIG. 29 depicts the spacer and joint of FIG. 28, the joint having been aligned by the spacer.

FIGS. 28-29 illustrate a spacer 5050 having non-parallel bone engaging surfaces 5052, 5054 forming a wedge shape. Any of the methods and apparatus of the disclosure may be used to align vertebrae 300, 302, together with a wedge shaped spacer, such as spacer 5050. FIGS. 28-29 further illustrate that a therapeutic alignment is any alignment which is beneficial for the patient, whether natural and expected, or unique to an individual patient.

Figure 30:
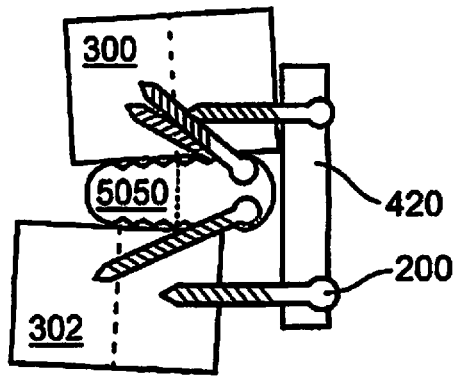
FIG. 30 is a diagram of the joint and spacer of FIG. 28, and a cross-section of a plate of the disclosure, the spacer and plate cooperative to align the joint.

FIG. 30 illustrates reduction of bones 300, 302, with an assembly of the disclosure which includes a wedge shaped spacer 5050, and which uses the apparatus and method described above with respect to FIGS. 28-29, although other methods and apparatus as described herein may be used as would be understood by a medical practitioner.

Figure 31:
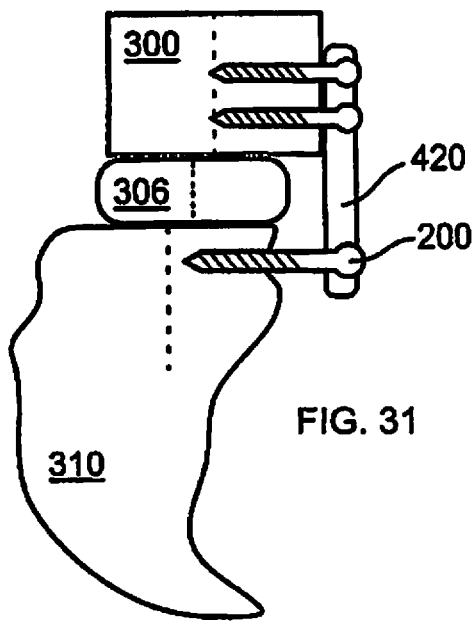
FIG. 31 depicts a joint of the body, in this example the L5 and S1 vertebrae, and a cross-section of a plate of the disclosure connected to both vertebrae.
Figure 32:
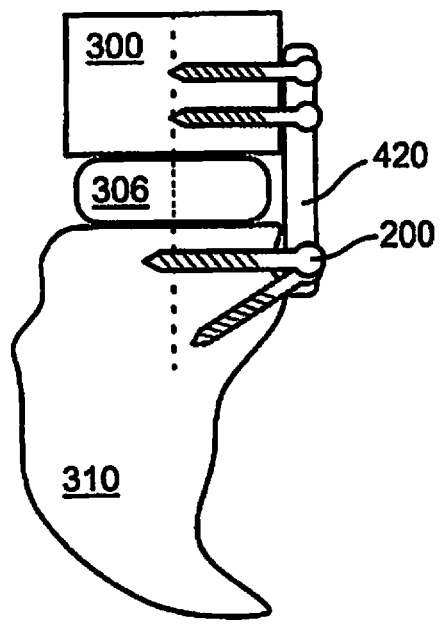
FIG. 32 depicts the joint of FIG. 31, aligned by the plate, the plate further secured to the joint.

FIGS. 31-32 illustrate an apparatus and method similar to that of FIGS. 26-27 as employed at the L5-S1 level. While the sacrum 310, in particular, is illustrated here, it should be understood that vertebrae 300, 302, 310 may be any vertebrae or jointed surface of the body.

FIGS. 33-34 also illustrate an apparatus and method similar to that of FIG. 26, however in this embodiment, screw 204 is provided with threads 206 which engage a nut 208 at one end, and body tissue at an opposite end. Screw 204 is passed through, or otherwise engages plate 420, for example with a notch (not shown), and is fastened to body tissue. Two nuts secured together may be employed at the end of screw 204 for engaging a driving tool, or alternatively, screw 204 may be provided with a tool engaging surface, for example a hex, slotted, or Phillips engagement (not shown). If such engagement interferes with passage of nut 208 onto screw 204, nut 208 may be passed first along the bone engaging end of screw 204. After screw 204 is engaged with body tissue, in this example sacrum 310, and plate 420, nut 208 may be driven upon screw 204 and in engagement with plate 420, to move plate 420 and sacrum 310 together, either by displacing sacrum 310, vertebra 300, or a combination of both, until alignment is achieved, as shown in FIG. 34. After alignment, screw 204 may be reduced in length to avoid interference with body tissue, particularly after an opening in the body is closed. While screw 204 may be severable with a tool, for example a saw or cutting shears, one or more weakened regions 210 may be provided along the length of screw 204 to facilitate breaking off or otherwise removing an excess length of screw 204.

FIGS. 35-36 illustrate reduction of vertebrae 300, 302 using an elongate screw 212 which passes through the intervertebral space, connecting two adjacent bones. Threads 214 are formed on a distal end of screw 212, whereby after passing through and seating within vertebra 300, screw 212 may thereafter freely rotate in connection with vertebra 300. Screw head 216 is sized to block movement of screw through the cortical bone of vertebra 300. Once screw 212 is seated within vertebra 300, threads 214 continue to engage tissue of vertebra 302, thereby drawing vertebra 302 towards vertebra 300, and into a therapeutic alignment. After alignment, screw 212 may be left within the body, or removed, optionally replaced by alternative means for maintaining an alignment of vertebrae 300, 302.

With reference to FIGS. 37-38, assembly 128 includes a ratchet tool 6080 having a lever 6082 attached to a toothed rack, pawl, or gear 6084, engaged with one or more mating racks 6086. A drawbar 6088 is releasably engaged with vertebra 300, for example with angled teeth 6090. More particularly, teeth 6090 may be slidingly positionable with respect to vertebra 300 in a first direction, and engageable with tissue associated with vertebra 300 in a second direction, whereby vertebra 300 may be reduced in the second direction when drawbar 6088 is engaged and displaced. Drawbar 6088 is connected to rack 6086, whereby movement of rack 6086 causes a corresponding movement of drawbar 6088, whereby a medical practitioner may move an engaged vertebra in a second direction. In one embodiment, gear 6084 is rotatable about a fixed point 6092 with respect to vertebra 300, whereby movement of lever 6082 causes reduction of vertebra 300 with respect to fixed point 6092.

In another embodiment, a second drawbar 6088A engages a second vertebra 302, however in this embodiment angled teeth 6090A slidingly engage vertebra 302 in the second direction, and engage tissue associated with vertebra 302 in the first direction. Rack 6086A additionally engages gear 6084, whereby movement of lever 6082, causes movement of drawbars 6088, 6088A in opposite directions, thereby applying a moving force to both vertebrae 300, 302, but in opposing directions, promoting relative alignment of vertebrae 300, 302.

In FIGS. 39-40, an assembly of the disclosure includes a spacer 5058 having two mating portions 5060, 5062, each releasably or fixedly engageable with a vertebra at a bone engaging surface 5064, 5066. Mating surfaces 5070, 5072 are connected to move relative to each other, joined by a sliding fastener 5074. An adjusting device 5076 is associated with sliding fastener 5074 to retain a relative position of mating portions 5060, 5062, together with engaged vertebra 300, 302, once sliding alignment is carried out. In the embodiment illustrated, adjusting device 5076 includes a threaded rod 5078 engageable within a channel 5080, 5082 disposed in each of mating surfaces 5070, 5072, however it should be understood that other mechanical couplings are contemplated within the disclosure, as would be understood by one skilled in the art, for example including a riveted or molded coupling. Advantageously, threaded rod 5078 may be threadingly received within mating surfaces 5070, 5072, whereby a distance between vertebrae 300, 302, for example distraction, may also be carried out, in addition to reduction. Additional threaded nuts, or other fastener, not shown, may be used along threaded rod 5078 to secure adjusting device 5076 at a desired location along channel 5080, 5082.

Referring now to FIGS. 41-44, a wedge shaped spacer 5090 includes recessed or projecting engaging surfaces 5092. Spacer segments 5096, 5098 are sized and dimensioned to be connectible with facing portions of vertebrae 300, 302, and are provided with projecting or recessed engaging surfaces 5100 complementary to and mateable with engaging surfaces 5092. As spacer 5090 is inserted between vertebra 300, 302, a distraction of vertebra 300, 302 takes place due to the wedge shape, and the force with which spacer 5090 is inserted. When spacer 5090 is sufficiently inserted, engaging surfaces 5092 and 5100 will engage, initially in connection with one of segments 5096, 5098. Subsequently, the medical practitioner displaces or reduces one or both of vertebrae 300, 302 until they are therapeutically aligned. Manipulation of vertebrae 300, 302 may be carried out by engaging segments 5096, 5098 manually, or with a tool, for example using screws 218, or other engageable surface. Alternatively, or additionally, vertebrae 300, 302 may be directly manipulated.

Engaging surfaces 5092 and 5100 are positioned so that a complementary engagement takes place when a therapeutic alignment of segments 5096, 5098, and spacer 5090 has been accomplished. Accordingly, after alignment, an engagement is made between engaging surfaces 5100 of segment 5098 and engaging surfaces 5092 of spacer 5090, and engaging surfaces 5100 of segment 5096 and spacer 5090, thereby aligning all of vertebra 300, segment 5096, spacer 5090, segment 5098, and vertebra 302.

After alignment, body tissue associated with vertebrae 300, 302, such as ligaments 308, maintain engagement of segments 5096, 5098, and spacer 5090. Additionally, spacer 5090 may be further secured to either or both of segments 5096, 5098 by fasteners, including adhesives or threaded fasteners. Similarly, segments 5096, 5098 may be secured to body tissue.

FIGS. 43-44 illustrate alternative configurations of the embodiment of FIGS. 41-42, in which segment 5096A or 5098A have a sloped shape, adapted to complement a wedge shape of spacer 5090. In this embodiment, a relative angular alignment of vertebrae 300, 302 is not changed, however an anterior-posterior displacement may be corrected. Alternatively, an increased angular alignment may be achieved by the use of an alternative angular profile of segment 5096B and or segment 5098B, as shown in FIG. 44.

With reference to FIGS. 45-46, any tool of the disclosure may be used to address a displacement of vertebrae 300, 302, to form an assembly including a dynamic spacer 5110 which is used to distract a joint formed between vertebrae 300, 302. In this embodiment, exemplary tool 6010, as described with respect to FIGS. 8-10, is used to reduce vertebrae 300, 302. During or after the reduction of a displacement of vertebrae 300, 302, distraction is achieved using spacer 5110, which may be resilient, or which may be expanded by the introduction of a gas or fluid, for example purified air or sterile saline. After distraction, any known form of stabilization may be employed, for example including a plate, rod, or cable. Spacer 5110, as with any spacer of the disclosure, may be provided with a surface texture and or a releasable therapeutic substance which, for example, promotes bone growth.

In FIGS. 47-48, an assembly of the disclosure is illustrated which is similar to the assembly and method described with respect to FIGS. 33-34, but is configured to cooperate with spacer 5120. More particularly, spacer 5120, which may have the form of any spacer of the disclosure, is secured to plate 420 by any known means, including screw 202, as illustrated. This further stabilizes vertebrae 300, 302, and maintains a therapeutic location of a spacer. In a further embodiment, a connection between spacer 5120 and plate 420 is partly or substantially rigid, preserving at least a portion of a natural range of motion.

The assembly of FIGS. 49-50 is analogous to plate 420 and screw 204, and functions in a like manner. However, plate 420 is connected to, or formed together with, spacer 5124. In this manner, a superior-inferior disposition of vertebrae 300, 302 may be achieved during insertion of spacer 5124, followed by a reduction in an anterior-posterior direction during tightening of nut 208. This embodiment further provides for fixation of adjacent vertebrae. Either or both of extensions 5126, 5128 may be flexible, to preserve at least a portion of a natural range of motion.

Figure 51:
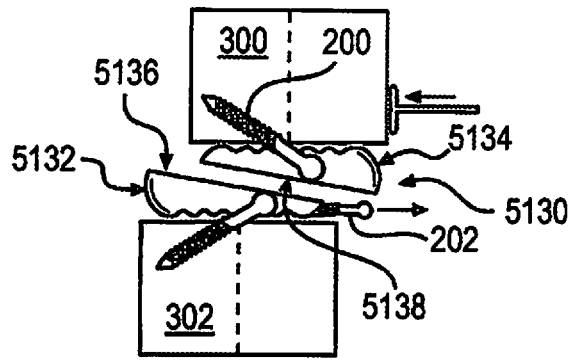
FIG. 51 is a diagram of the joint of FIG. 1, a cross-section of a spacer of the disclosure with ramped segments, and an indication of an application of force to align the joint.
Figure 52:
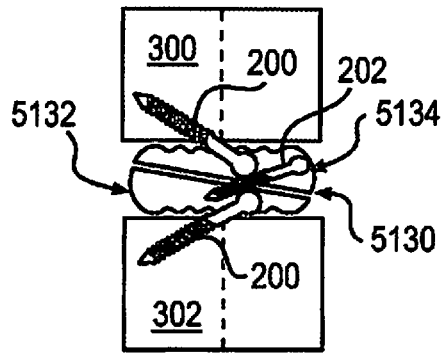
FIG. 52 depicts the joint and spacer of FIG. 51, the joint having been aligned using the spacer, the spacer segments fastened together after alignment.

In FIGS. 51-52, a spacer 5130 includes two segments 5132, 5134, each connectable to a vertebra 300 or 302. Each segment 5132, 5134 has a ramped surface 5136, 5138 complementary to the other, whereby as segments 5132, 5134 are moved relative to each other into an overlapped conformity, a height of spacer 5130 is increased. In this manner, segments 5132, 5134 may be assembled into an intervertebral space, engaged with body tissue of adjacent vertebrae, and then slide along ramped surfaces 5136, 5138 into overlapping conformity, whereby reduction and distraction can both be accomplished simultaneously. A sufficient engagement may be achieved between segments 5132, 5134 and the respective vertebrae 300, 302 to which they are attached, by projections 5140, or adhesive. An engagement may be further secured by the use of one or more bone screws 200.

In the embodiment of FIGS. 51-52, reduction may be carried out by apparatus and methods of the disclosure. In one embodiment, a fastener, for example screw 202 in FIG. 51, may be used to attach to a tool. In FIG. 52, vertebrae 300, 302 are aligned, and segments 5132, 5134 are secured to each other, for example using adhesive or other fastener, such as screw 202, illustrated. In another embodiment, screw 202 may freely rotate within a slot (not shown) in segment 5134, and be threadably received within segment 5132, whereby reduction and distraction may be carried out, at least in part, by rotating screw 202.

Figure 53:
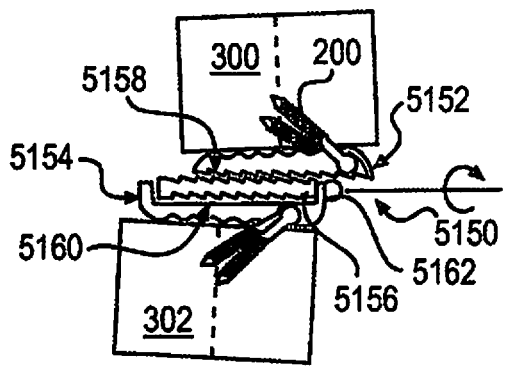
FIG. 53 is a diagram of the joint of FIG. 1, and a cross-section of an adjustable segmented spacer of the disclosure, the spacer including a rotatable screw operative to align the segments.
Figure 54:
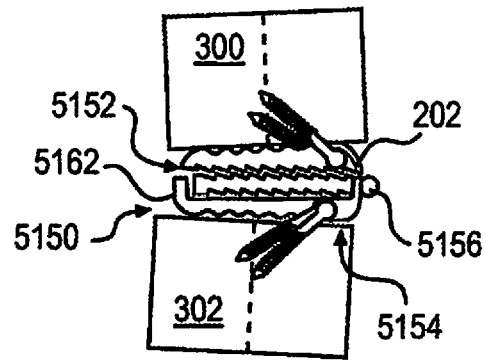
FIG. 54 depicts the joint and spacer of FIG. 53, the joint having been aligned using the spacer, the segments of the spacer fixed by a fastener.

Referring to FIGS. 53-54, an embodiment includes a spacer 5150 having segments 5152, 5154, each connectable to a vertebra 300 or 302. A threaded shaft 5156 is disposed between segments 5152 and 5154, threadably engaging threaded surface 5158 of segment 5152, and slidingly engaging surface 5160 of segment 5154. As shaft 5156 is rotated, shaft 5156 engages threaded surface 5158, driving segment 5152 into alignment with segment 5154, thereby aligning the attached vertebrae 300, 302. One or more shaft collars 5162 prevents movement of shaft 5156 out of engagement with segment 5154. An alignment of segments 5152 and 5154 may be maintained with a fastener, for example screw 202, thereby maintaining an alignment of vertebrae 300, 302.

In some embodiments, the threaded shaft 5162 can be configured to allow for a movable upper member (e.g., such as a movable segment 5152) to move relative to a stationary lower member (e.g., such as a stationary segment 5154). The movable upper member can be attached to a superior vertebral body, while the stationary lower member can be attached to an inferior vertebral body.

Figure 55:
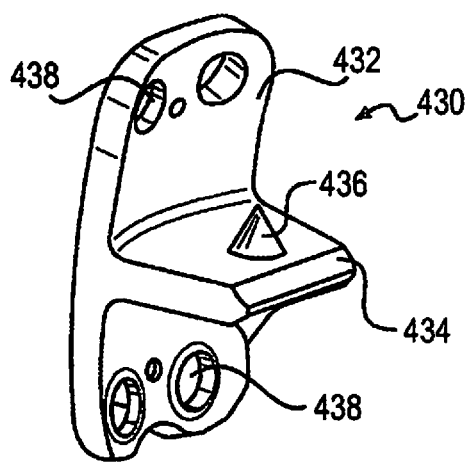
FIG. 55 is a side view of a combined plate, spacer, and fasteners of the disclosure.
Figure 56:
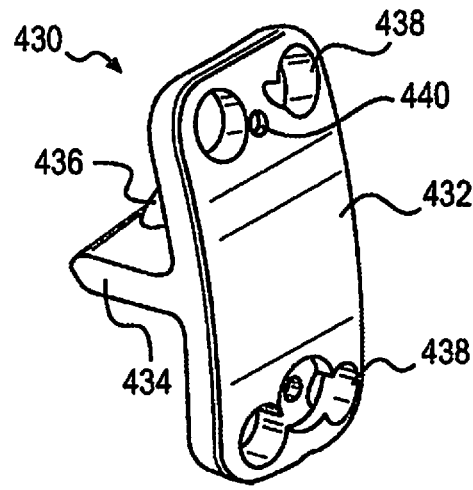
FIG. 56 is a perspective view from the top of the device of FIG. 55.
Figure 78:
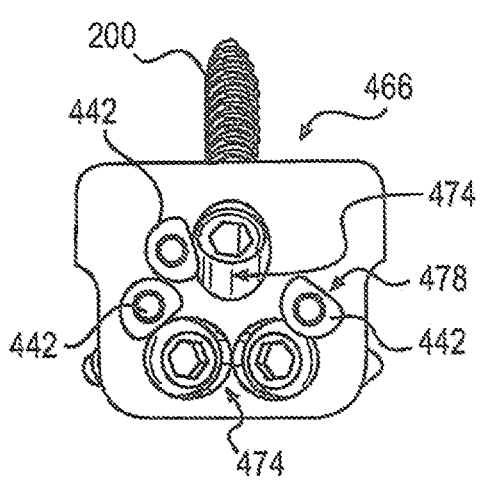
FIG. 78 is a front view of the device of FIG. 74, illustrating locking pins.

In FIGS. 55-56, a plate 430 may be therapeutically used alone, or in combination with other devices of the disclosure, to provide stability to adjacent bones, for example vertebrae 300, 302. Plate 430 includes an exterior plate 432, and a plate extension 434 sized and dimensioned to project into an articulating region of the joint when the exterior plate is fastened to adjacent bones. Plate extension 434 further includes one or more projections 436 configured to pierce body tissue of adjacent bones within the articulating space, thereby securing a location of the adjacent bones, plate extension 434, and exterior plate 432, relative to each other. In this manner, after adjacent bones, for example bones 300, 302 are aligned in accordance with the disclosure, plate 430 may be inserted and secured within the intervertebral space to prevent, through engagement of projections 436, to prevent a migration or movement of vertebrae 300, 302 out of alignment. To further secure vertebrae 300, 302 and plate 430 relative to each other, bone screws 200 may be passed through apertures 438. A locking screw or pin 442 (an example is shown in FIG. 78) may be attached at lock location 440, to prevent reversal of screws 200 after installation.

Figure 57:
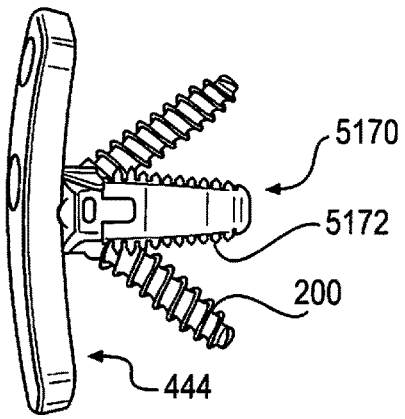
FIG. 57 is a side view of an alternative combined plate, spacer and fasteners of the disclosure.
Figure 58:
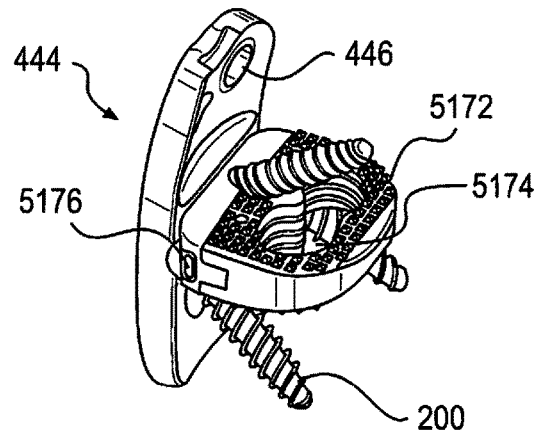
FIG. 58 is top perspective view from the top of the device of FIG. 57.
Figure 59:
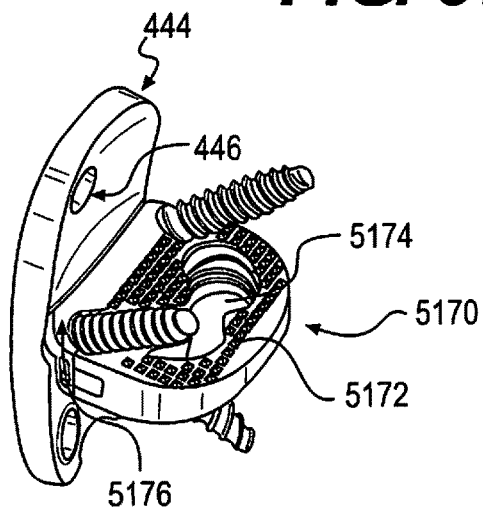
FIG. 59 is an alternate top perspective view from the top of the device of FIG. 57.

In FIGS. 57-59, spacer 5170 is connectable to plate 444 by one or more fasteners, for example one or more screws 202 (not shown). One or more bone screws 200, or other fastening method of the disclosure, may be used to secure spacer 5170 in a joint space, for example in the intervertebral space between vertebrae 300, 302, prior to connecting plate 444. In this manner, additional space is provided for accessing the joint space. Plate 444 may thereafter be connected to spacer 5170. As an alternative to connecting plate 444 to spacer 5170 directly, one or more bone screws 200 may be passed through apertures 446 in plate 444, through apertures 5176 in spacer 5170, and into body tissue. After connection to spacer 5170, plate 444 may be connected to opposing sides of the joint, for example to cortical bone of vertebrae 300, 302. In this manner, an alignment of vertebrae 300, 302 may be preserved, as vertebrae 300, 302 are connected to each other at least through a mutual connection to plate 444, and additionally via spacer 5170, either through screws 200, and/or via projections 5172, or by bone ingrowth, for example through an aperture 5174 in spacer 5170. Finally, additional support is achieved by connecting spacer 5170 and plate 444, as described.

Figure 60:
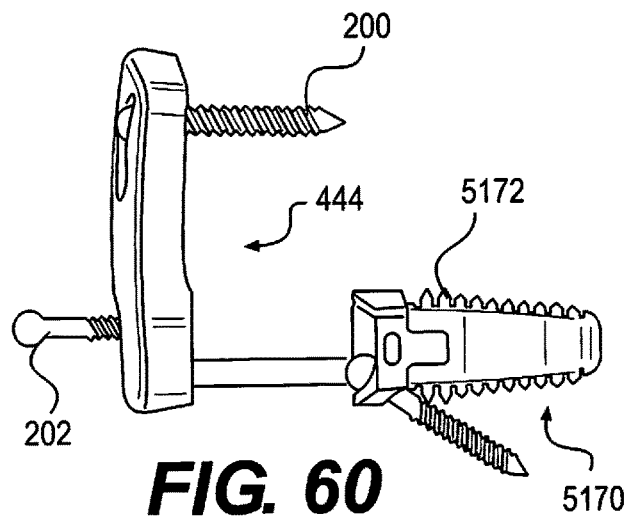
FIG. 60 is a side view of a mateable plate and spacer of the disclosure.
Figure 61:
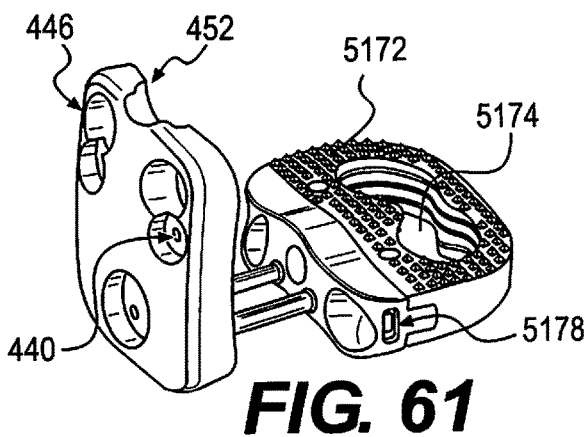
FIG. 61 is a perspective view of the device of FIG. 60.

In FIG. 60, spacer 5170 is utilized, as described with respect to FIGS. 57-59, however plate 448 is provided with one or more projections or posts 450 which mateably engage spacer 5170. In this manner, spacer 5170 may be inserted to a desired depth within the joint space, and post 450 may be engaged with spacer 5170 to prevent a change in angular disposition between plate 448 and spacer 5170. In the embodiment shown, plate 448 is further connectable with one of the bones of the joint, for example vertebra 300, however plate 448 could extend in an opposite direction to be more easily connectable with a bone on the opposite side of the joint, for example vertebra 302. One or more bone screw apertures 446 and lock locations 440 may be provided as described herein. A fastener, for example screw 202, may be used to further engage plate 444 and spacer 5170, and to prevent movement of spacer 5170 within the joint space. Tool engagement surfaces 452, 5178 upon plate 448 and spacer 5170, respectively, are configured to facilitate releasable attachment of a surgical tool to an implanted device of the disclosure, for case of manipulation.

Figure 62:
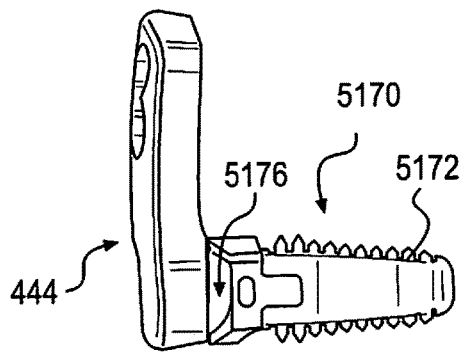
FIG. 62 is a side view of the device of FIG. 60, the plate and spacer mutually assembled in conforming relationship.
Figure 63:
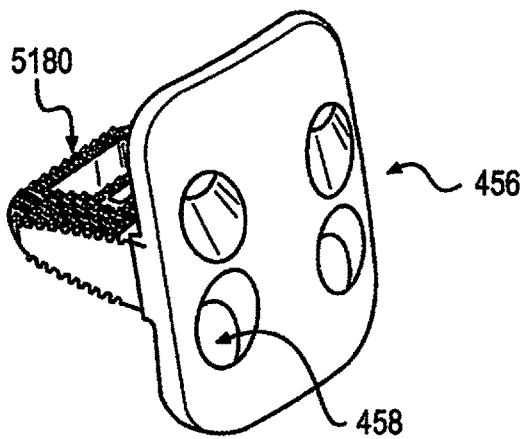
FIG. 63 is a front perspective view of a combined plate and spacer of the disclosure.

In another embodiment of the disclosure, shown in FIG. 63, plate 456 connects to spacer 5180 by a fastener as disclosed herein, or by a dovetail or other shaped connection. Spacer 5180 is not provided with apertures 5176 (as shown for example in FIGS. 58 and 62), or if they are present, they are not required to be used. More particularly, plate 456 provides for anchoring both plate 456 and spacer 5180 to the joint, using angulated apertures 458, through which bone screws or other fastener may be passed to connect with bones of the joint, for example vertebrae 300, 302. Reduction of vertebrae 300, 302 may be accomplished as disclosed elsewhere herein, or plate 456 may be fastened to first one vertebra 300, and then as bone screws are subsequently rotated into bone of vertebra 302, plate 456 and vertebrae 302 are drawn together, positioning vertebrae 300, 302 into alignment.

Figure 64:
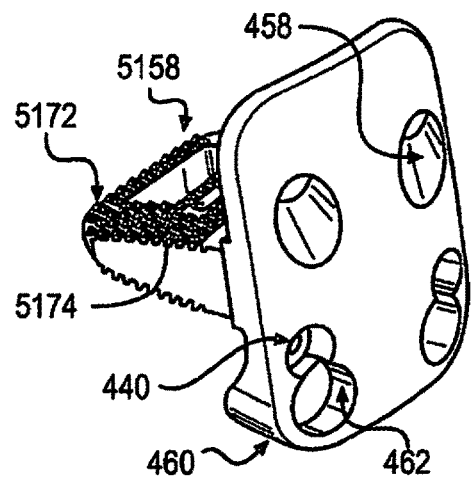
FIG. 64 is a front perspective view of a combined plate and spacer of the disclosure, the plate provided with a shaped projection.
Figure 65:
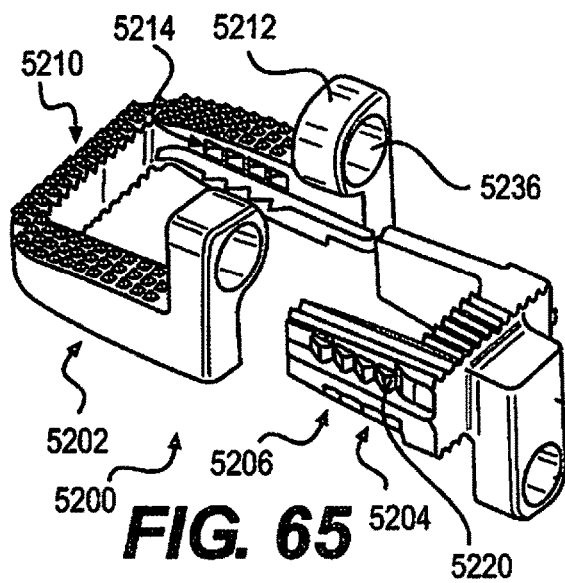
FIG. 65 is a perspective illustration of spacer of the disclosure formed of mateable segments.
Figure 66:
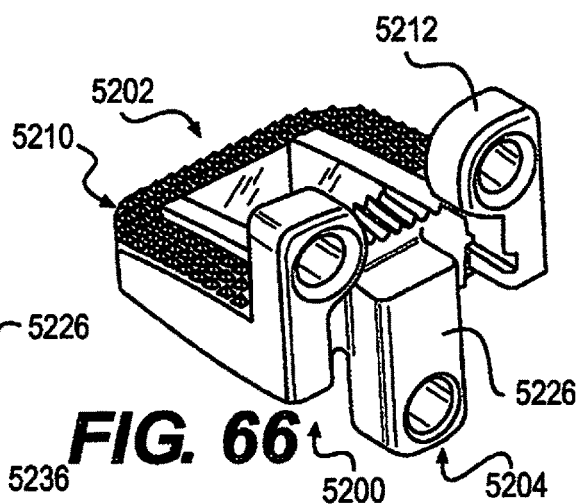
FIG. 66 is a perspective view of the spacer of FIG. 65, the segments mated.
Figure 67:
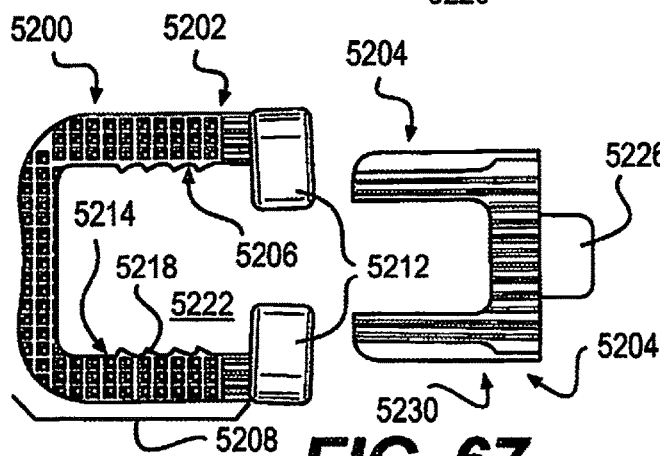
FIG. 67 is a top view of the device of FIG. 65.
Figure 68:
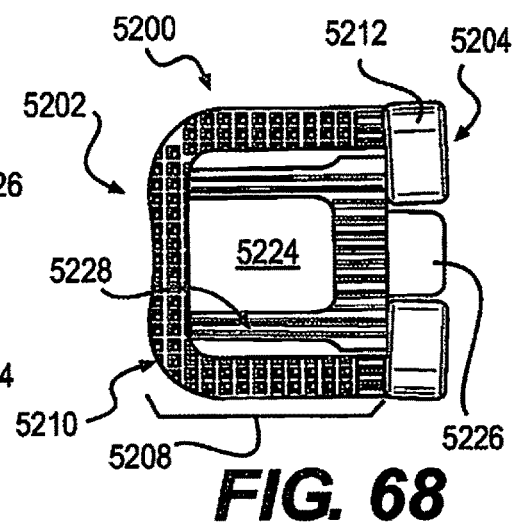
FIG. 68 is a top view of the device of FIG. 66.

The embodiment of FIG. 64 is similar to the embodiment of FIG. 63; however plate 460 includes one or more shaped projection 464 that function to conform to the particular shape of a bone to which it is engaged, such as the sacrum, to form a better, more stable fit, and to produce a smaller implanted profile. Locking locations 440 are advantageously provided to prevent reversal of a fastener inserted through bone screw apertures 446.

In FIGS. 65-68, spacer 5200 includes two mateable segments 5202, 5204 which fasten together using a ratchet interface 5206. Segment 5202 forms an intervertebral spacer portion 5208 advantageously including projections 5210 which engage body tissue in the joint space to reduce a likelihood of movement of bones of the joint relative to segment 5202. One or more mounting extensions 5212 extend from intervertebral spacer portion 5208 and are configured, for example with one or more apertures 5236, to engage a fastener to secure segment 5202 to body tissue, for example by passage of a bone screw 200 through mounting extension 5212 and into cortical bone of one of vertebrae 300, 302.

Segment 5204 slideably engages segment 5202, formed to project into and nest within a groove 5214 on an inner face 5216 of intervertebral spacer portion 5208. Adjacent to, or incorporated within groove 5214 and mating portions of segment 5204, are ramped engagement surfaces 5218, 5220 which admit passage past each other as segment 5204 is slidingly engaged with segment 5202 to pass into an interior passage 5222 of segment 5202, and which prevent a reversal of this engagement of segments 5202, 5204. Engagement surfaces 5218, 5220 form an interference fit with respect to each other, and are permitted to engaged successive mutually facing ramped surfaces by a resilient bending of the material of segments 5202, 5204. It should be understood that groove 5214 may be formed within segment 5204, and segment 5202 could be formed to extend thereinto.

Segment 5204 is similarly provided with an interior passage 5224, whereby the mated segments form an opening between vertebrae 300, 302, through which bone growth may therapeutically take place, for further stabilization, and to promote tissue health. Longitudinal projections 5228 may advantageously be formed upon an upper and lower face of an intervertebral spacer portion 5230, aligned along the direction of mateable sliding of segment 5204 with segment 5202, and similarly serve to provide a stable engagement between segment 5204 and body tissue into which projections 5228 project.

Segment 5204 further has one or more mounting extensions 5226 extending from an intervertebral spacer portion 5230. As with mounting extensions 5212, mounting extensions 5226 are configured to engage a fastener to secure segment 5202 to body tissue, for example by passage of a bone screw 200 through mounting extension 5212 and into cortical bone of one of vertebrae 300, 302.

To correct for a misalignment of bones of the joint, segment 5202 is first securely connected to a bone of the joint, for example vertebra 300, using mounting extensions 5212. Next, segment 5204 is mounted to segment 5202 by sliding segment 5204 partially along a length of groove 5214, until mounting extension 5226 contacts tissue of the misaligned bone, for example vertebra 302. Next, using any of the methods described herein, including manually pushing vertebra 302, segment 5204 is driven further into mateable engagement with segment 5202, whereby engagement surfaces 5218, 5220 cooperate to prevent reversal of the engagement, and maintain segments 5202, 5204 at a desired extend of mutually overlapped engagement. Through engagement with segments 5202, 5204, bones of the joint are maintained in relative alignment. Thus secured, no additional plates or stabilizing implants are required, although they may be used as deemed therapeutically beneficial for the patient.

Segments 5202, 5204 may be moved relative to each other by attaching a lever between segments 5202, 5204, using a method or device as described herein.

A fastener, including for example a screw or adhesive, may be used to further secure segments 5202, 5204 in mutual conformity, or to secure segments 5202, 5204 to body tissue. Bone growth materials, therapeutic drugs, or other beneficial substances may be placed within interior passage 5224.

Spacer 5240 of FIGS. 69-73 is similar to the embodiment of FIGS. 65-68, with certain distinctions, described herein. Elements having a similar function, therefore, will be similarly numbered, and reference may be had to the foregoing discussion for a description of their structure and function.

Segments 5242, 5244 form a sliding connection therebetween formed by interlocking projections 5246 and recesses 5248. A variety of interlocking forms may be produced by interlocking projection 5246 and recess 5248, including for example a mortise and tenon, dovetail, and half-dovetail type sliding joint. If a pair of interlocking projections 5246, 5248 are provided, as illustrated, they may be configured to cooperate to form a secure sliding connection. For example, each projection may be provided with a single angular face, on relatively opposing sides of each of two projections 5246.

As may be seen in FIGS. 72-73, in spacer 5240A, projection 5246 and recess 5248, of segments 5242A, 5244A, are oriented to be slidable along an axis that is transverse with respect to an anterior-posterior axis of the body, when extensions 5212 are secured to an anterior face of vertebrae 300, 302. In this manner, alignment of the vertebrae may be carried out along the coronal plane, as opposed to along the sagittal plane, as illustrated for spacers 5200 and 5240, when the respective spacer is implanted and affixed to the body. Projection 5246 and recess 5248 may thus be aligned along any axis of the body, to address a particular pathology.

Once a therapeutic alignment has been achieved, segments 5242A, 5244A are advantageously secured in relation to each other, to preserve an intended alignment of connected bones. As may be seen in FIG. 72, an optional set screw 5250 may be used to secure segments 5242, 5244, or any segmented device herein, or alternatively, other fasteners of the disclosure may be used, such fasteners including adhesive. Further, ramped engagement surfaces 5218, 5220, shown in FIGS. 65-68, may be provided. In addition, or in the alternative, other bone fixation devices may be used in combination with spacer 5240, 5240A, or any other device of the disclosure.

It should be understood that either segment 5242 or 5244 may be formed with a projection 5246 or recess 5248, with the mating segment assuming the alternate profile.

Referring now to FIGS. 74-78, a spacer 5260 includes a coupling formed by a groove 5262 into which a complementary projection 468 of plate 466 is inserted. Groove 5262 and projection 468 may be shaped in any of a variety of mating configurations, including, as examples, a mortise and tenon, or a dovetail. It should be noted that foregoing coupling may be provided for other assemblies of a spacer and plate, in this disclosure; likewise, spacer 5260 and plate 466 may be connected using alternate methods of the disclosure.

Figure 74:
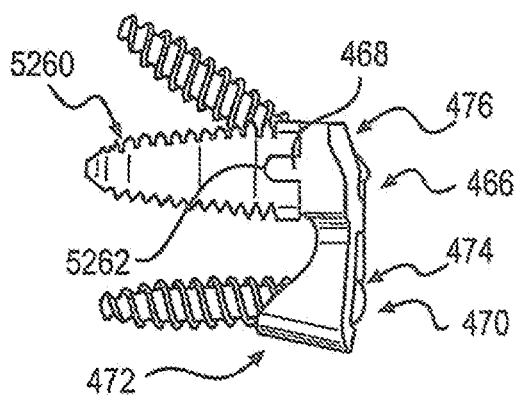
FIG. 74 is a side view of a combinable spacer, plate, and fasteners of the disclosure, the plate provided with a shaped projection, the fasteners disposed at an angle.
Figure 79:
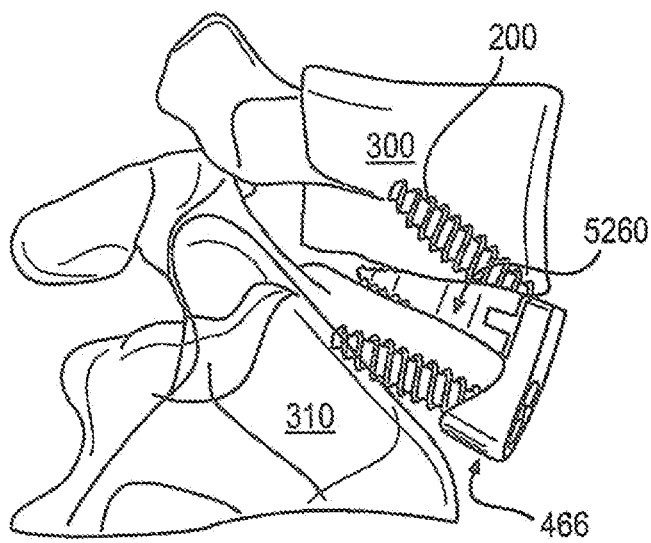
FIG. 79 is a side view of the device of FIG. 74, implanted within a spine.

In an embodiment, spacer 5260 and plate 466 are inserted into a space between bones of a joint, for example in the intervertebral space, until a plate extension 470 contacts bone of the joint, for example bone of vertebra 302. In the embodiment of FIG. 74, plate extension 470 has a projecting shape 472 sized and dimensioned to contact a surface of the sacrum 310, as shown in FIG. 79, although projecting shape 472 may be adapted for contacting a different surface of the body, as shown for example in plate 466A of FIG. 75.

Figure 75:
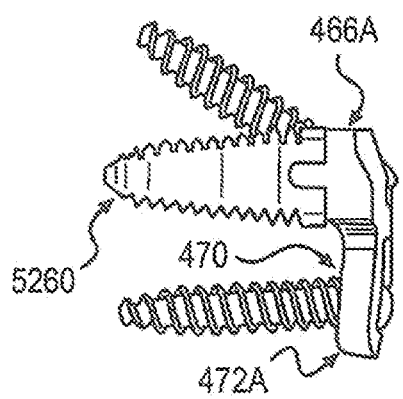
FIG. 75 is a side view of a combinable spacer, plate, and fasteners of the disclosure, the plate provided without the shaped projection illustrated in FIG. 74, the fasteners disposed at an angle.
Figure 76:
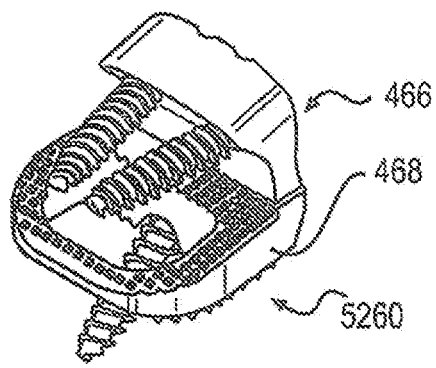
FIG. 76 is a bottom perspective view of a combinable spacer, plate, and fasteners of the disclosure, the plate provided with a shaped projection, the fasteners disposed at a converging angle.
Figure 77:
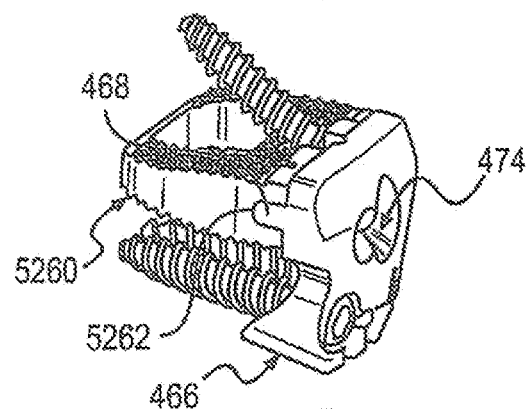
FIG. 77 is a top perspective view of the device of FIG. 76.

In FIGS. 76-77, it may be seen that bone screws 200, passed through plate apertures 474 of plate 466, may form angles along their longitudinal dimension that mutually converge. This is advantageous, for example, to ensure that screws 200 obtain purchase in supportive tissue, that they do not extend vertebral body, and or that they do not interfere with body tissue that must be protected. In FIGS. 74-75 and 78, it may be seen that screws 200 may also form divergent angles. Plate apertures 474 may be formed to guide screws 200 along intended angles, or may be polyaxial, whereby the medical practitioner may choose a therapeutically effective angular disposition of screw 200, or other fastener.

FIGS. 74-79 further illustrate that implanted devices of the disclosure may be formed with chamfered edges 476, to facilitate implantation, and to reduce interference with body tissue. Additionally, where a screw or other fastener passes through a device of the disclosure, it is advantageous to ensure that the fastener does not back out from engagement with the device or body tissue, which could lead to injury or failure of the device. FIG. 78 illustrates a locking screw or pin 442 operative to prevent substantially movement of screw 200, or other elongated fastener, in a direction reverse to an installation direction, after implantation. A reduced profile portion 478 of pin 442 admits passage of screw 200, when pin 442 is rotated so that reduced profile 478 faces aperture 474, as shown in a lower left screw of FIG. 78. After a head portion of screw 200 has passed reduced profile 478, pin 442 may be rotated so that a non-reduced portion of pin 442 blocks a path of screw 200, as shown for the lower right screw.

Figure 80:
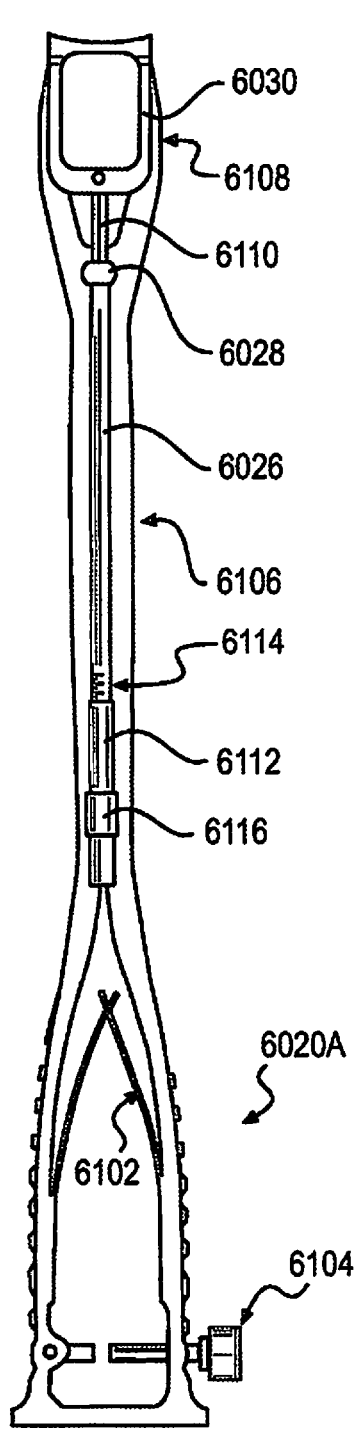
FIG. 80 is an illustration of an insertion and alignment tool in accordance with the disclosure.

FIGS. 80-84 illustrate tool 6020A, a variation of tool 6020 of FIGS. 16-18, illustrated in use together with the embodiment of FIG. 74. In FIG. 80, it may be seen that tool 6020A includes handles, advantageously including a biasing element 6102, and a lock 6104 to maintain handles in a desired disposition. A pivot 6106 enables movement of handles to effect a corresponding movement of grippers 6108, shaped and dimensioned to cooperate with tool engagement surfaces 5178, which are advantageously formed upon spacer 5260 and or plate 466, for this purpose.

The functions of engagement surface 6030, push rod 6026, and guide 6028 have been explained with respect to FIGS. 16-18. It may further be seen that push rod 6026 is formed with a groove 6110 engageable with a projection of guide 6028, operative to thereby prevent rotation of push rod 6026 and connected engagement surface 6030. Additionally visible is an internally threaded collar 6112, cooperative with a threaded external portion 6114 of push rod 6026, threaded collar 6112 rotatably fixed within support 6116 to advance or withdraw push rod 6026 to effectuate movement of contacted body tissue. A proximal tool engaging end 6118 of threaded collar 6112 may be engaged and driven by a tool, for example a powered drill or t-handle, to rotate collar 6112. As rotation and reduction take place along the same axis, control of the reduction is optimized.

Figure 81:
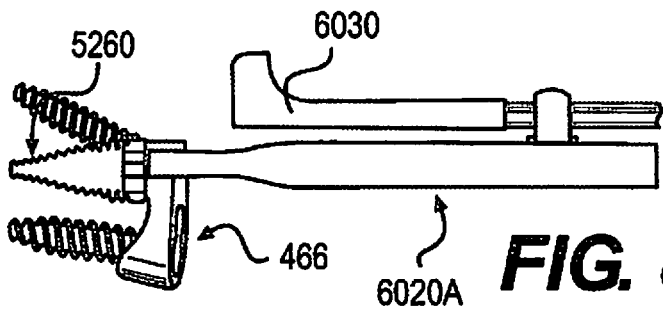
FIG. 81 depicts a side view of the tool of FIG. 80 gripping the device of FIG. 74.
Figure 82:
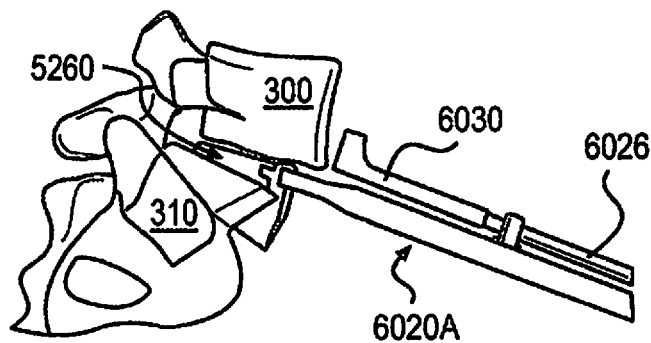
FIG. 82 depicts the tool and device of FIG. 81, the tool having inserted the device into a spine, the device fastened to the S1 vertebra.
Figure 83:
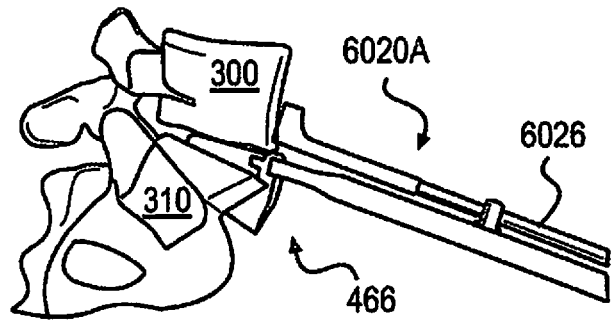
FIG. 83 depicts the tool and device of FIG. 81 having aligned vertebrae of the spine.
Figure 84:
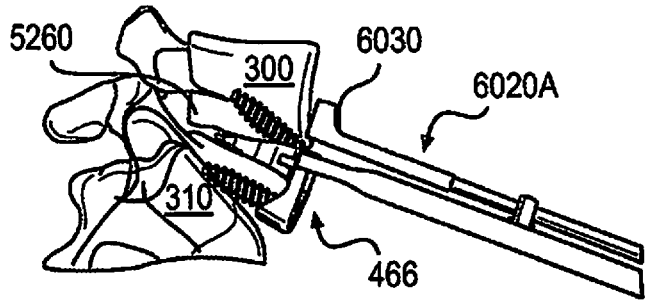
FIG. 84 depicts the tool and device of FIG. 83, the device fastened to the L5 vertebra.

In FIGS. 16-18, a threaded connection 6024 is formed between tool 6020 and spacer 5030. In the embodiment of FIGS. 80-84, grippers 6108 engage an external surface of spacer 5260. Alternatively, both grippers 6108 and threaded connection 6024 may be formed. FIG. 81 illustrates an assembly of spacer 5260 and plate 466 gripped by tool 6020A. In FIG. 82, tool 6020A has been used to push the assembly into a disc space formed between vertebra 300 and sacrum 310. Subsequently, screws 200 have been inserted into the caudal vertebra, or sacrum 310. In FIG. 83, engagement surface 6030 has been advanced, through rotation of threaded collar 6112, to engage and urge vertebrae 300 posteriorly with respect to sacrum 310, into therapeutic alignment. In FIG. 84, one or more screws 200 are inserted into the cephalad bone, vertebra 300, to thereby fix an alignment of vertebra 300 and sacrum 310.

Figure 85A:
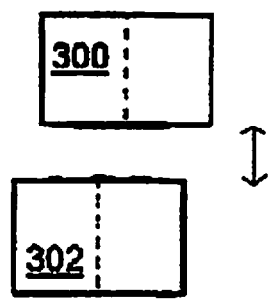
FIGS. 85A-85C depict a method of inserting a spacer in accordance with the disclosure.
Figure 85B:
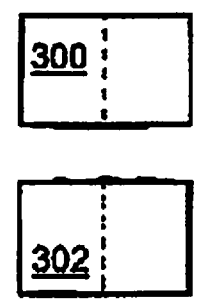
Figure 85C:
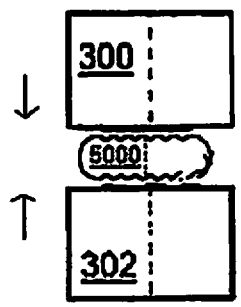

FIGS. 85A-85C depict a method of inserting a spacer in accordance with the disclosure. In FIG. 85A, adjacent vertebrae 300, 302 are being distracted. In some embodiments, the vertebrae are overdistracted to provide space for a spacer, such as any of those shown in the above embodiments. In FIG. 85B, after overdistracting the vertebrae, vertebra 302 can be aligned with vertebra 300. Any of the devices, systems and methods discussed above can be used to align the upper vertebra 302 with the lower vertebra 300. In FIG. 85C, after alignment of the vertebrae, a spacer 5000 with surface protrusions can be inserted into the disc space between the overdistracted vertebrae. Once the spacer is inserted into the disc space, the vertebrae 300, 302 can be compressed over the spacer, thereby completing the surgical procedure.

Figure 86:
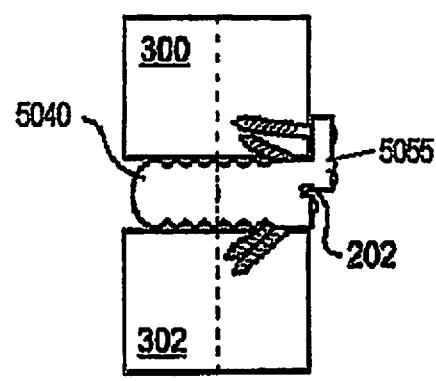
FIG. 86 depicts a side view of a combinable spacer, plate and fasteners of the disclosure, the plate provided with an upper lip.

FIG. 86 depicts a side view of a combinable spacer 5040, plate having an upper lip 5055 and fasteners 202 of the disclosure. Advantageously, the upper lip 5055 of the plate can contact the upper vertebra 300, such that when the combined spacer and plate is forced anteriorly, the upper lip 5055 can help to push the upper vertebra 300 into alignment with the lower vertebra.

Figure 87:
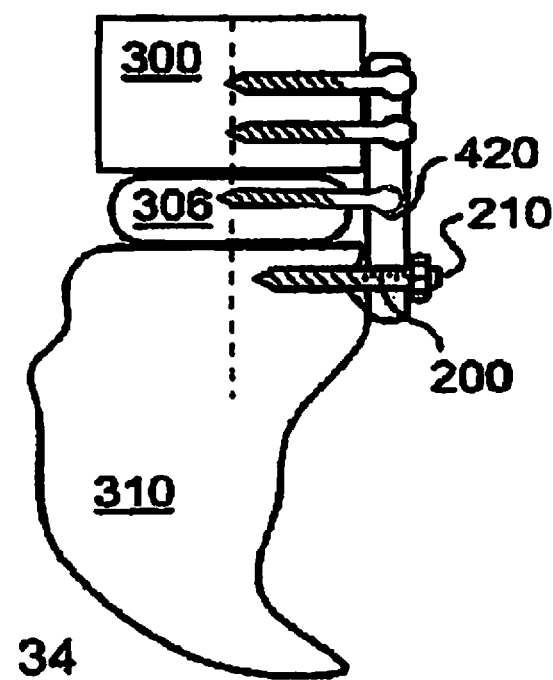
FIG. 87 depicts a joint of the body, in this example the L5 and S1 vertebrae, and a cross-section of an alternative plate of the disclosure connected to both vertebrae.

FIG. 87 depicts a side view of an alternative plate and spacer combination, similar to that shown in FIG. 34. In this embodiment, one or more screws 200 can be provided through the plate 420. The screws 200 can be aligned such that at least one enters a vertebral body, while at least one other enters into a disc 306.

The devices and methods of the disclosure enable delivering and implant and reducing spondylolisthesis from an anterior approach, although other approaches are possible. More particularly, the disclosure provides for delivering an implant and reducing the spondylolisthesis using a single tool, thereby at least reducing separate approaches into the body, and reducing time required for the procedure, for the benefit of the patient and the medical practitioners, while reducing risks and costs. Additionally, by performing insertion and reduction using a single implant, and by using a single tool, accuracy is improved, and manipulation of body tissue is minimized.

Spacers, plates, and fasteners of the disclosure may be formed with biocompatible materials, of sufficient purity, including for example PEEK (polyether ether ketone), titanium, stainless steel, or a cobalt chromium alloy. Other polymers, metals, alloys, or composite materials may alternatively be used, as known in the art, or hereinafter developed. A radiopacifier may be added to devices of the disclosure to improve visibility under imaging. Devices of the invention may be formed by extrusion, milling, forging, casting, molding, or any other method advantageously used for the materials selected and the structure intended.

It should be understood that, in the various embodiments illustrated and described herein, an assembly may include any or all of a spacer, plate, tool, and or fasteners, and although all such elements may be shown in a particular illustration, for brevity and compactness, one or more such elements may be eliminated in a particular medical application, as would be understood by one skilled in the art. For example, an implant such as a spacer may not require separate fasteners. Alternatively, a disc 306 may be healthy, and not in need of replacement, or a spacer may be used without a plate.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for therapeutically aligning two adjacent bones on opposite sides of a joint space, comprising:
    distracting the two adjacent bones;
    providing a device including:
        a first segment having a mounting extension and an intervertebral spacer portion configured to be disposed in the joint space, the intervertebral spacer portion including a posterior section, a first side section extending anteriorly from one end of the posterior section and a second side section extending anteriorly from the other end of the posterior section to face the first side section, wherein the posterior section, the first side section and the second side section define a three sided portion;
        a second segment configured to mate with the first segment, the second segment including an aperture, an anterior section, a third side section extending posteriorly from one end of the anterior section and a fourth side section extending posteriorly from the other end of the anterior section to face the third side section, the third and fourth side sections configured to respectively slidably mate with the first and second side sections of the first segment;
        a first fastener configured to be received in the mounting extension; and
        a second fastener configured to be received in the aperture;
    non-reversibly mating the first segment with the second segment via a ratchet interface disposed on the first, second, third and fourth side sections;
    inserting the intervertebral spacer portion into the joint space;
    securing a first fastener through the mounting extension and into one of the two adjacent bones; and
    securing a second fastener through the aperture and into one of the two adjacent bones.

2. The method of claim 1, wherein the first segment includes projections to engage the joint space.

3. The method of claim 1, wherein the second segment is configured to slidably engage the first segment.

4. The method of claim 3, wherein the second segment is configured to nest into a groove on an inner face of the intervertebral portion.

5. The method of claim 4, wherein the groove includes engagement surfaces.

6. The method of claim 5, wherein the engagement surfaces engage the second segment.

7. The method of claim 6, wherein the engagement surfaces are ramped.

8. The method of claim 7, wherein the engagement surfaces are configured to provide an interference fit between the second segment and the intervertebral spacer portion.

9. A method for therapeutically aligning two adjacent bones on opposite sides of a joint space, comprising:
    distracting the two adjacent bones;
    providing a device including:
        a first segment having a plurality of mounting extensions and a U-shaped intervertebral spacer portion configured to be disposed in the joint space;
        a second segment configured to mate with the first segment, the second segment including an aperture;
        a first set of fasteners each configured to be received in one of the plurality of mounting extensions; and
        a second fastener configured to be received in the aperture;
    non-reversibly mating the first segment with the second segment via a ratchet interface disposed on the first, second, third and fourth side sections;
    inserting the intervertebral spacer portion into the joint space;
    securing each first set of fastener through one the mounting extensions and into one of the two adjacent bones; and
    securing a second fastener through the aperture and into one of the two adjacent bones.

10. The method of claim 9, wherein the first segment includes projections to engage the joint space.

11. The method of claim 9, wherein the second segment is configured to slidably engage the first segment.

12. The method of claim 11, wherein the second segment is configured to nest into a groove on an inner face of the intervertebral portion.

13. The method of claim 12, wherein the groove includes engagement surfaces.

14. The method of claim 13, wherein the engagement surfaces engage the second segment.

15. The method of claim 14, wherein the engagement surfaces are ramped.

16. The method of claim 15, wherein the engagement surfaces are configured to provide an interference fit between the second segment and the intervertebral spacer portion.

* * * * *